(12) United States Patent
Carlson et al.

(10) Patent No.: US 11,906,404 B2
(45) Date of Patent: Feb. 20, 2024

(54) AEROSOL AND VAPOR ENHANCED SAMPLE MODULE

(71) Applicant: Signature Science, LLC, Austin, TX (US)

(72) Inventors: Micah Carlson, National Harbor, MD (US); Danielle Dickinson, Alexandria, VA (US)

(73) Assignee: Signature Science, LLC, Austin, TX (US)

( * ) Notice: Subject to any disclaimer, the term of this patent is extended or adjusted under 35 U.S.C. 154(b) by 560 days.

(21) Appl. No.: 16/612,465

(22) PCT Filed: Mar. 27, 2018

(86) PCT No.: PCT/US2018/024687
§ 371 (c)(1),
(2) Date: Nov. 11, 2019

(87) PCT Pub. No.: WO2018/176060
PCT Pub. Date: Sep. 27, 2018

(65) Prior Publication Data
US 2021/0278321 A1    Sep. 9, 2021

Related U.S. Application Data

(60) Provisional application No. 62/475,886, filed on Mar. 24, 2017.

(51) Int. Cl.
G01N 1/24       (2006.01)
G01N 1/22       (2006.01)
(Continued)

(52) U.S. Cl.
CPC .............. *G01N 1/24* (2013.01); *G01N 1/2208* (2013.01); *G01N 1/2273* (2013.01);
(Continued)

(58) Field of Classification Search
CPC ................ G01N 1/24; G01N 1/2208; G01N 2001/2223; G01N 1/2273; G01N 33/0011; G01N 33/0027; G01N 2001/022
(Continued)

(56) References Cited

U.S. PATENT DOCUMENTS 4,972,957 A * 11/1990 Liu ................... G01N 15/06
                                                       55/510
5,425,263 A *  6/1995 Davies ............... G01V 9/007
                                                       73/28.06
(Continued)

FOREIGN PATENT DOCUMENTS

HU    1500115 A2 *  2/2018  ............... G01N 1/22
JP    4085941 B2 *  5/2008  ........... G01N 1/2214
(Continued)

OTHER PUBLICATIONS

F.D. Lopez-Hilfiker et al, A novel method for on-line analysis of gas and particle composition: description and evaluation of a Filter Inlet for Gases and AEROsols (FIGAERO), Atmos. Meas. Tech. Discuss., 6, 9347-9395, 2013 www.atmos-meas-tech-discuss.net/6/9347/2013/, 2013, pp. 9347-9395 (Year: 2013).*
(Continued)

Primary Examiner — Stephanie E Bloss
Assistant Examiner — Kevin C Butler
(74) Attorney, Agent, or Firm — John A. Fortkort; Fortkort & Houston PC

(57) ABSTRACT

A sampling system is disclosed which comprises a collection chamber equipped with an inlet and first and second outlets; a pump which creates a flow of fluid into said inlet from the ambient environment, wherein said collection chamber divides the flow of fluid into a first major flow of fluid along which flows along a first flow path between said inlet and said first outlet, and a second minor flow of fluid which flows
(Continued)

along a second flow path between said inlet and said second outlet; a collection surface disposed within said collection chamber and within the second flow path such that particles in the flow of fluid into said inlet impinge on said collection surface; a heater which vaporizes particles that collect on said collection surface; and an analyzer which analyzes the composition of the fluidic flow through said second outlet.

20 Claims, 30 Drawing Sheets

(51) Int. Cl.
  *G01N 33/00* (2006.01)
  *G01N 1/02* (2006.01)
(52) U.S. Cl.
  CPC ..... *G01N 33/0011* (2013.01); *G01N 33/0027* (2013.01); *G01N 2001/022* (2013.01); *G01N 2001/2223* (2013.01)
(58) Field of Classification Search
  USPC .................................................... 73/31.01
  See application file for complete search history.

(56) References Cited

U.S. PATENT DOCUMENTS

| | | | | |
|---|---|---|---|---|
| 7,299,710 | B2 * | 11/2007 | Syage | G01N 1/2205 73/31.03 |
| 7,339,165 | B2 * | 3/2008 | Donaldson | H01J 49/0472 250/284 |
| 8,178,045 | B2 * | 5/2012 | Cambron | G01N 1/405 422/89 |
| 8,539,840 | B2 * | 9/2013 | Ariessohn | G01N 1/2202 73/860 |
| 8,569,691 | B2 * | 10/2013 | Cambron | G01N 1/405 250/281 |
| 8,723,111 | B2 * | 5/2014 | Syage | H01J 49/049 250/423 P |
| 8,771,613 | B2 * | 7/2014 | Martin | G01N 1/405 73/25.05 |
| 11,181,456 | B2 * | 11/2021 | Myers | G01N 15/1463 |
| 11,221,288 | B2 * | 1/2022 | Brown | G01N 15/1434 |
| 11,333,593 | B2 * | 5/2022 | Myers | G01N 1/2273 |
| 11,391,613 | B2 * | 7/2022 | Speldrich | G03H 1/0005 |
| 2005/0058575 | A1 * | 3/2005 | Ishikawa | G01N 1/2214 422/83 |
| 2006/0006327 | A1 * | 1/2006 | Donaldson | H01J 49/0472 250/284 |
| 2007/0034024 | A1 * | 2/2007 | Syage | G01N 1/4005 73/864.34 |
| 2010/0120167 | A1 * | 5/2010 | McGill | G01N 1/40 436/178 |
| 2011/0203931 | A1 * | 8/2011 | Novosselov | G01N 1/2202 250/382 |
| 2011/0314902 | A1 * | 12/2011 | Dantler | G01N 1/14 73/28.01 |
| 2013/0082172 | A1 * | 4/2013 | Syage | H01J 49/162 250/288 |
| 2013/0091963 | A1 * | 4/2013 | Syage | G01N 1/02 73/863.11 |
| 2013/0239704 | A1 * | 9/2013 | Syage | G01N 1/4005 73/863.23 |
| 2014/0060155 | A1 * | 3/2014 | Hering | G01N 1/2202 73/863.22 |
| 2014/0151543 | A1 * | 6/2014 | Nagano | H01J 49/0422 250/288 |
| 2014/0260542 | A1 * | 9/2014 | Nagano | G01N 1/2211 73/28.04 |
| 2020/0333218 | A1 * | 10/2020 | Gorbunov | G01N 1/4022 |
| 2021/0278321 | A1 * | 9/2021 | Carlson | G01N 1/2208 |
| 2022/0365052 | A1 * | 11/2022 | Gentner | G01N 30/20 |

FOREIGN PATENT DOCUMENTS

| | | | | |
|---|---|---|---|---|
| JP | | 6061738 B2 * | 1/2017 | ......... G01N 1/2211 |
| WO | | 2016147018 A1 | 9/2016 | |

OTHER PUBLICATIONS

Matt Shipman, "Researchers find new way to control light with electric fields", Phys. Org (May 25, 2017).
Milton, HE, Nagaraj, M, Kaur, S et al., Field-induced refractive index variation in the dark conglomerate phase for polarization-independent switchable liquid crystal lenses. Applied Optics, 53 (31). 7278-7232. ISSN 1559-128X (2014).
M. Zeki Kurt, "Refractive Index Change Produced by the Electro-Optical Effect in LiTaO3", Mathematical and Computational Applications, vol. 3, No. 1, pp. 17-26 (1998).

* cited by examiner

Sample Module Controller

| | | | | |
|---|---|---|---|---|
| Screen Setpoint (C) | 40 | [40] | Flash | OFF | Flash Fault | OK | Screen Temp (C) | 46 |
| Housing Setpoint (C) | 40 | [40] | Pump | ON | Screen T Fault | OK | Housing Temp (C) | 38 |
| Pressure Setpoint (mBar) | 100 | [100] | Screen Heater | OFF | Screen Heat Fault | OK | Filter Pressure (mBar) | 48 |
| Flash On Time (sec) | 15 | [10] | Housing Heater | OFF | Pump Fault | OK | Nozzle Pressure (mBar) | 69 |
| Collect Time (sec) | 60 | [60] | Response | OK | Nozzle Fault | OK | | |
| | | | Packets | 215 | Filter Fault | OK | | |
| Test Pump [0] | | | | | Flow Fault | OK | | |
| ☐ Test Lamp | | | | | | | | |
| | | | | | ☐ Logging | | [Disconnect] | |
| Mode  Flow Through  [Flow Through ▼] | | | | | | | [WiFi] | |

AEROSOL AND VAPOR ENHANCED SAMPLE MODULE

CROSS-REFERENCE TO RELATED APPLICATIONS

The present application is a national stage filing of PCT/US2018/024687, filed on Mar. 27, 2018, having the same title, the same inventors, and which is incorporated herein by reference in its entirety, which claims the benefit of priority from U.S. Provisional Application No. 62/475,886, filed on Mar. 24, 2017, which has the same title and the same inventors, and which is incorporated herein by reference in its entirety.

FIELD OF THE DISCLOSURE

The present disclosure relates generally to sampling devices, and more particularly to a method and apparatus for the continuous and simultaneous concentration, collection, and vaporizing of dry and liquid aerosol particles and vapors for chemical analysis.

BACKGROUND OF THE DISCLOSURE

The separation and collection of particles from an air stream is applicable to a variety of fields. In particular, the detection and identification of liquid and solid aerosols for their chemical constituents is of interest in a variety of applications. These include, for example, the detection of hazardous chemicals and threat vectors, and various applications in the pharmaceutical industry and the environmental sciences.

Various methods of inertial collection have been employed in the art to collect particulates into liquids or onto surfaces for subsequent analysis. Examples of virtual impactors which employ these methodologies may be found, for example, in U.S. Pat. No. 3,901,798 (Peterson), U.S. Pat. No. 4,670,135 (Marple et al.), U.S. Pat. No. 4,767,524 (Yeh et al.), U.S. Pat. No. 5,425,802 (Burton et al.) and U.S. Pat. No. 5,533,406 (Geise). Typical virtual impaction systems entrain the size selected material into an airstream, where they are then impacted on a surface or are collected on media for subsequent analysis.

Inertial impactors are commonly used in biological detection and for inertial separation and classification by a variety of techniques. These technologies typically separate the particles form the bulk gas, resulting in a higher proportion of particles than is commonly found in the background environment. Common collection methods include impactors (collection on a surface), virtual impactors (collecting particles into a lower flow stream), impingers (collecting particles into a liquid), and filtration (pulling particles from a flow using a combination of inertial impaction and diffusion).

Impaction systems are typically designed to collect and concentrate particles in a central location. Virtual impactors concentrate particles into a lower volume based on a variety of well-known design factors, such as gas viscosity or particle density.

SUMMARY OF THE DISCLOSURE

In one aspect, a sampling system is provided which comprises a collection chamber equipped with an inlet and first and second outlets; a pump which creates a flow of fluid into said inlet from the ambient environment, wherein said collection chamber divides the flow of fluid into a first major flow of fluid which flows along a first flow path between said inlet and said first outlet, and a second minor flow of fluid which flows along a second flow path from said inlet and through said second outlet; a collection surface disposed within said collection chamber and within the second flow path such that particles in the flow of fluid into said inlet impinge on said collection surface; a heater which vaporizes particles that collect on said collection surface; and an analyzer which analyzes the composition of second flow of fluid that emerges from said second outlet.

BRIEF DESCRIPTION OF THE DRAWINGS

FIG. 11 is a screenshot of a page generated by an embodiment of a software application which may be utilized to control an aerosol and enhanced sample module of the type disclosed herein.

DETAILED DESCRIPTION

Figure 1:
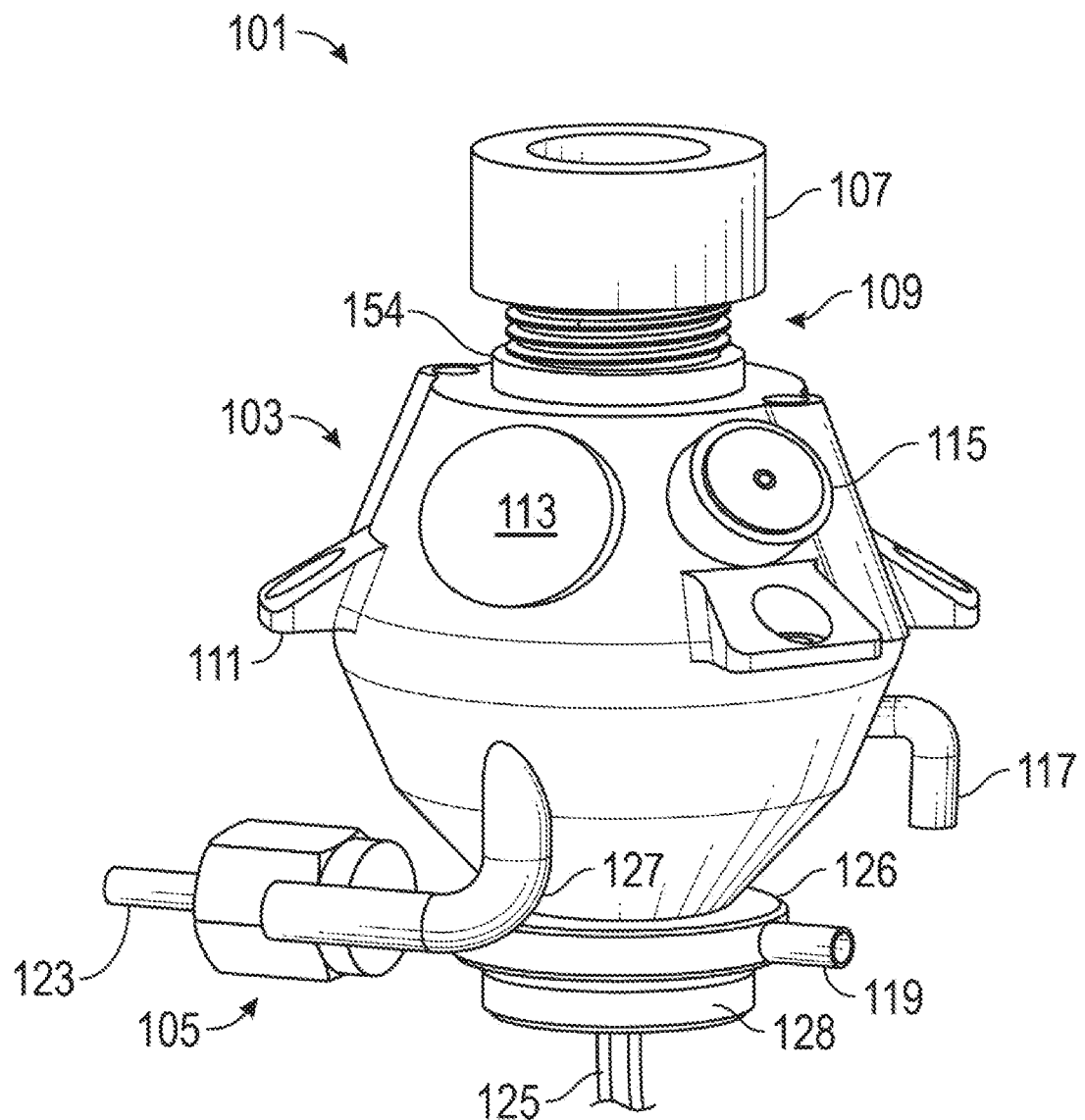
FIGS. 1-2 are illustrations of an embodiment of the aerosol and enhanced sample module disclosed herein. Some of the flexible design features of the aerosol and enhanced sample module are indicated.

An aerosol and vapor enhanced sample module is disclosed herein. The module has a porous and/or sorbent coated collection surface that enables the simultaneous collection and preconcentration of particles and vapors, the subsequent vaporization of the collected materials via application of thermal energy and ambient pressure reduction, and the subsequent analysis of the vaporized materials by a chemical detection system. The collected material that accumulates on the collection surface transfers resultant vapor-only materials through the porous collection surface into a minor flow gas for subsequent detection and identification by a chemical detector system. A prefilter, such as a traditional filter or size-selecting inertial separator, may be employed to prevent larger particles from entering the vaporization region.

In a preferred embodiment, the aerosol and vapor enhanced sample module is equipped with an attachment impaction surface or virtual impaction receiver section to maintain proper alignment without stringent machining requirements. The collection surface (which is preferably a screen) is in fluidic communication with a desorption heater and minor flow sampling tube. The subunits of the impactor are preferably coupled with a thread-and-retainer mechanism. Such a mechanism allows for sufficient pressure to be applied to the outer edge of the collection surface to create a seal, thus ensuring that all collected vapor enters the chemical analysis stream. Preferably, the aerosol and vapor enhanced sample module includes a single step alignment to maintain concentricity without multiple machining steps to minimize fabrication tolerances required with exiting designs.

The sampling tube preferably includes a heat source (which may be, for example, an inductive, optical or resistive heating heat source) that applies sufficient energy to the collection surface to vaporize particulates collected thereon. The resulting vapors then pass through the collection surface into a low flow stream. This low flow stream is preferably further heated, thus significantly increasing the chemical transfer efficiency. In some embodiments, one or more additional energy sources (which may be the same as, or different from, the first heat source) may be utilized to provide sufficient energy to vaporize particles accumulated on the collection surface. The foregoing arrangement may be utilized to yield a highly concentrated, low volume air stream with concentrated vapors that originated from the heated particulates or from concentrated vapors.

Traditional vapor-based chemical threats are quickly becoming replaced with more advanced, solids-based toxic compounds. Most military and industrial real-time chemical detection systems are unable to identify these solids-based compounds. There is thus a need in the art for a universal sample collection and preparation system which is capable of collecting, concentrating and converting particulate-based chemicals from the ambient environment into a vapor stream for suitable analysis. There is also a need in the art for such a system which can also simultaneously collect and pre-concentrate vapors from the ambient environment, and then convert both types of materials into a single vapor bolus for subsequent analysis. There is further a need in the art for such a system which can implement the foregoing with high chemical transfer efficiency for subsequent optical, mass, and/or physical property-based measurement systems.

Embodiments of the aerosol and enhanced sample modules disclosed herein facilitate the rapid vaporization of these hard to detect chemicals. In a preferred embodiment, the aerosol and enhanced sample module enables aerosol concentration and detection using a novel secondary flow design to capture, concentrate, and volatilize liquid and solid aerosols impacted onto a porous surface for detection and identification by a variety of vapor detection technologies. Simultaneously, vapors from the incoming flow are pre-concentrated in the porous substrate using novel sorbent configurations that allow for high surface area, low thermal mass, low pressure drop surface designs.

A preferred embodiment of the aerosol and enhanced sample modules described here samples at a variable flow rate from 1 to 10 LPM, and concentrates an incoming sample by a factor of up to 100 times or more over the ambient concentration. The resultant, highly concentrated vapor is continually ported into a variable flow volume to pass to the detection system. The operation is analogous to continuous sampling, where the aerosol and enhanced sample module selectively collects the aerosol and immediately converts captured aerosols into vapors. Pulsed mode operation of the system is also possible. This mode increases the preconcentration factor for both aerosols and vapors, analogous to sorbent-based sampling techniques. The system is customizable at the design stage for cut points of 0.25 to 20 um particles, and retains some flexibility during operation by varying the sampling flow rate and/or using pulsed operation. The unit is configured to report and accept commands either via direct connection or wirelessly using an Internet of Things (IoT) based micro-Controller, ensuring maximum flexibility for remote monitoring and dynamic response in an integrated monitoring system.

Embodiments of the aerosol collection systems disclosed herein may be used for impaction or virtual impaction collection (and subsequent thermal and reduced ambient pressure induced desorption) for analysis by a multitude of optical or physical separation and detection technologies. Such separation and detection technologies include, but are not limited to, technologies such as Mass Spectrometry, Ion Mobility Spectrometry, Differential Mobility Spectrometry, Field Asymmetric Ion Mobility Spectrometry, Infrared Spectroscopy, Fourier Transform Infrared Spectroscopy, and Raman Spectroscopy.

Various collection systems are known to the art which are based on impaction, virtual impaction, and a combination of these techniques. However, embodiments of the impactors/virtual impactors disclosed herein have an improved design that addresses various infirmities in such prior art systems. Methodologies are also disclosed herein for the subsequent vaporization (preferably by either thermal desorption and/or ambient pressure reduction) of the collected material into a reduced volume gas for subsequent analysis by a chemical detection system.

The collection systems disclosed herein may be configured for inertial impaction to collect material on a porous heated collection surface, drawing a resultant vapor through the system. The virtual impaction system captures a higher percentage of particles in a low flow stream which are then thermally desorbed and allowed to pass through the collection surface. These systems may be designed for a specific cutpoint size. For example, these systems may be designed such that particles having dimensions larger than the cutpoint are collected or captured, while particles having dimension smaller than that point pass through. Preferably, particles will be first inertially separated by either the impactor or virtual impactor and then will be collected, depending on the final collection surface specifications. The collection surface may be designed to capture a variety of particles, depending on the tolerance of the detection system to particles or the desired collection size.

In a preferred embodiment of the collection systems disclosed herein, a unique configuration of impactor and virtual impactor designs are combined with a porous substrate. The collection surface is embedded with sorbent capability for the subsequent vaporization of collected and concentrated vapor and aerosol material into a low flow volume which may be passed directly to a chemical detection system. The chemical detection system may be capable of classification, quantification or identification of the resultant chemical signatures.

Systems and methodologies are also disclosed herein for continuously concentrating, collecting, and vaporizing dry and liquid aerosol particles and vapors for chemical analysis. Preferably, these systems may be operated in either a flow-through or pulsed-mode of operation, depending on concentration and detection time requirements. Those skilled in the art will appreciate that many chemical detection systems have implemented particle impaction, filtration and heat for collection and analysis. However, a preferred embodiment of the systems and methodologies disclosed herein combines a virtual impaction, collection surface and integrated heating and flow directing elements to facilitate low energy, continuous operation of the concentration system without clogging of the collection surface that typically occurs in prior art devices.

Figure 2:
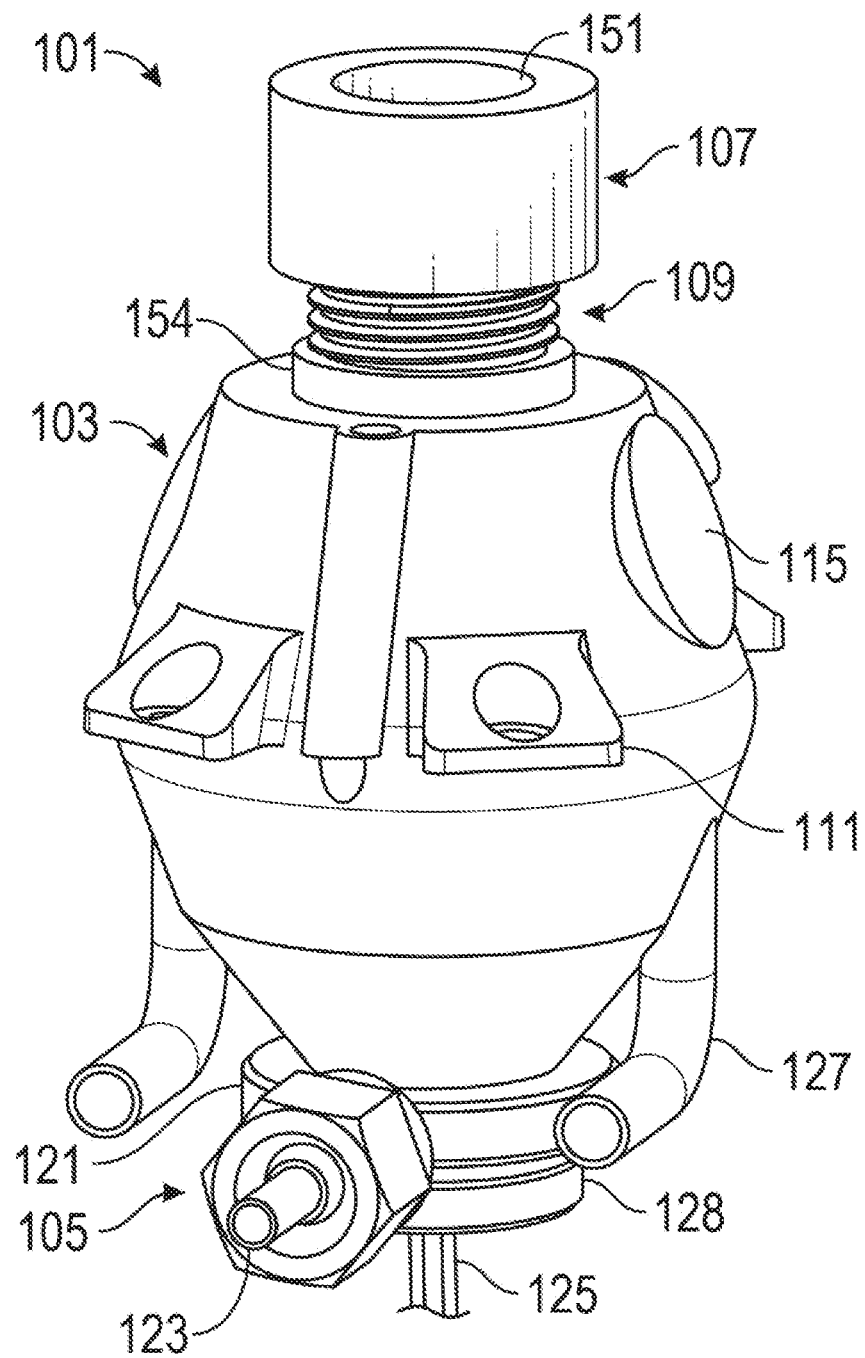

FIGS. 1-9 depict a first particular, non-limiting embodiment of an aerosol and vapor enhanced sample module in accordance with the teachings herein. With reference to FIGS. 1-2, the aerosol and vapor enhanced sample module 101 depicted therein comprises a housing 103 equipped with an inlet nozzle assembly 107, major exhaust lines 127 and a minor exhaust line 123 or gas sample transfer tube. The aerosol and vapor enhanced sample module 101 is also equipped with suitable power cords 125, 143 (see FIG. 3). During operation of the aerosol and vapor enhanced sample module 101, ambient air is drawn into the housing 103 via the inlet nozzle assembly 107, and exits the housing 103 via minor exhaust line 123 and major exhaust lines 127.

The internal sampling configuration and the flow paths for pulsed and flow through mode aerosol and vapor enhanced sample module 101 depicted in FIG. 1 may be appreciated with respect to FIGS. 5-9. As seen therein, the inlet nozzle assembly 107 of the aerosol and vapor enhanced sample module 101 depicted in FIG. 1 is equipped with an aerosol and vapor enhanced sample module intake 151 which is in fluidic communication with a conically shaped acceleration and focusing region 152. The acceleration and focusing region 152 serves to accelerate the incoming fluidic flow through an acceleration orifice 120 (see FIGS. 8-9) and focus it onto a (preferably porous) collection surface 124 which is heated by a heat source 113 (see FIGS. 5-9). The heat source is equipped with suitable electric leads 143 for resistive heaters (with or without integrated thermocouples).

Figure 5:
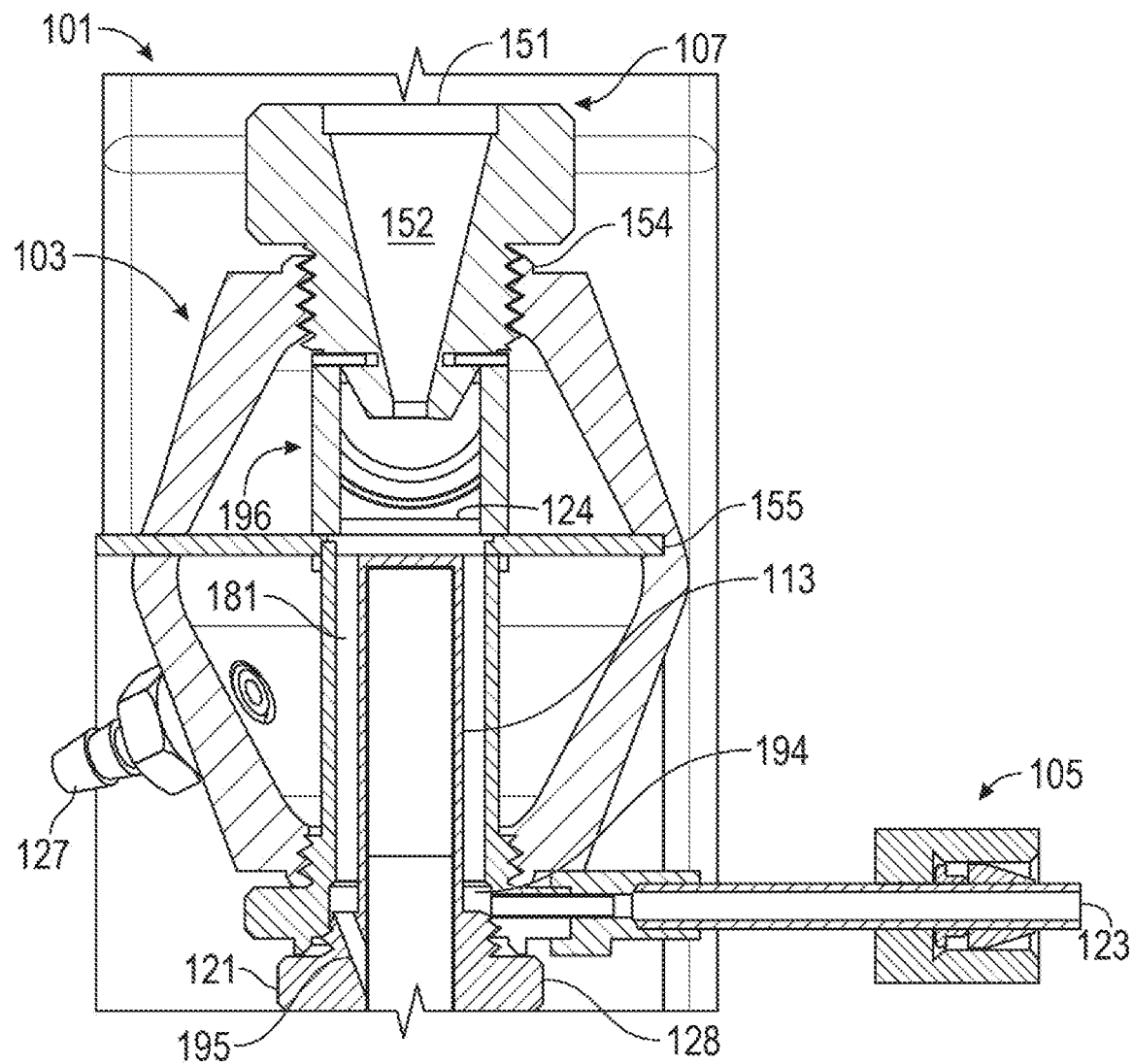
FIG. 5 is a cross-sectional view of the module of FIG. 1.
Figure 6:
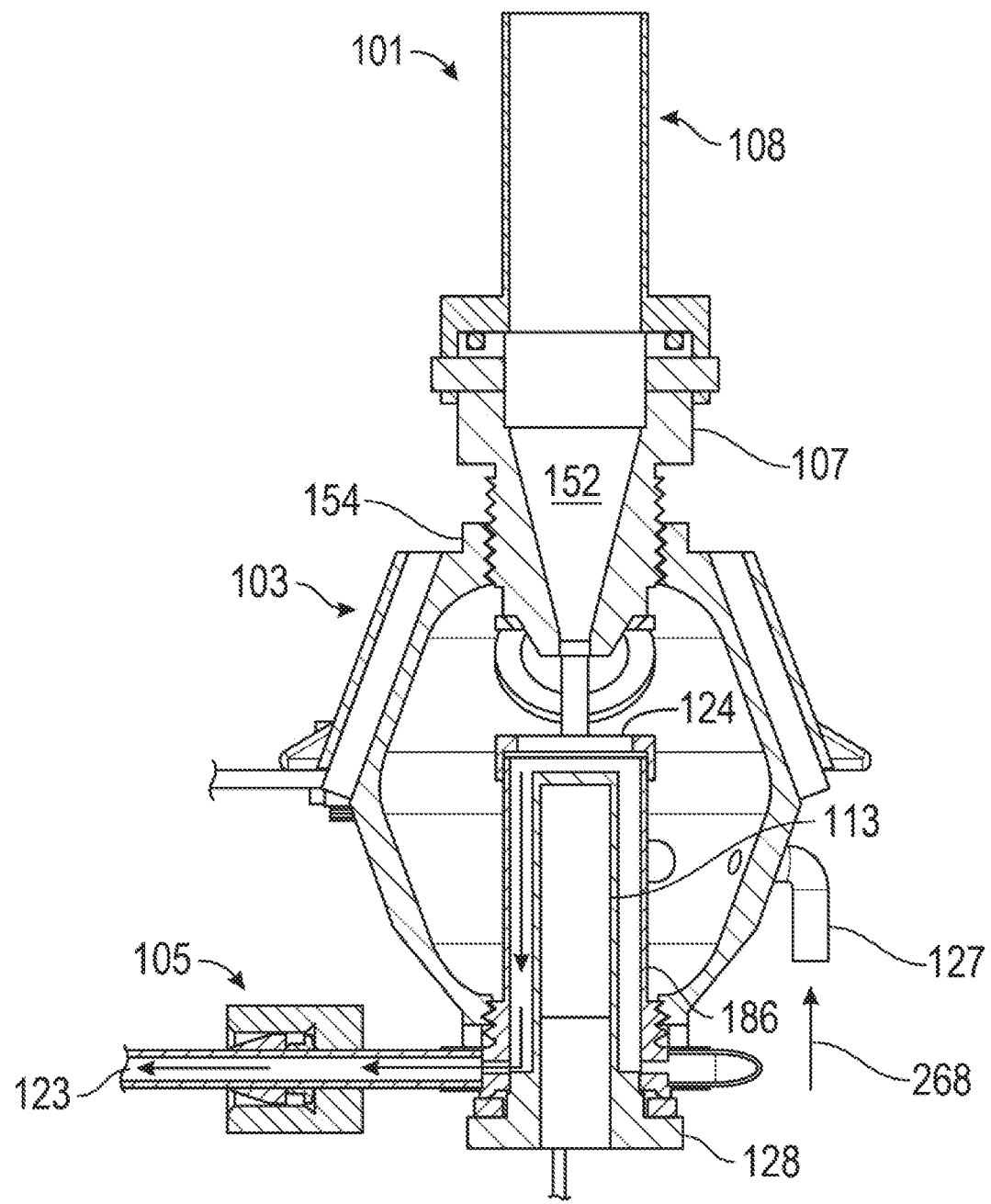
FIG. 6 is a cross-sectional view of the module of FIG. 3.

As seen in FIG. 5, the distance between the collection surface 124 and the orifice is set by a collection surface holder 196 (see FIG. 5). In the particular embodiment depicted, this distance may be adjusted by using collection surface holders of different dimensions, although embodiments are also possible in which the dimensions of the collection surface holder may be adjusted.

Figure 21:
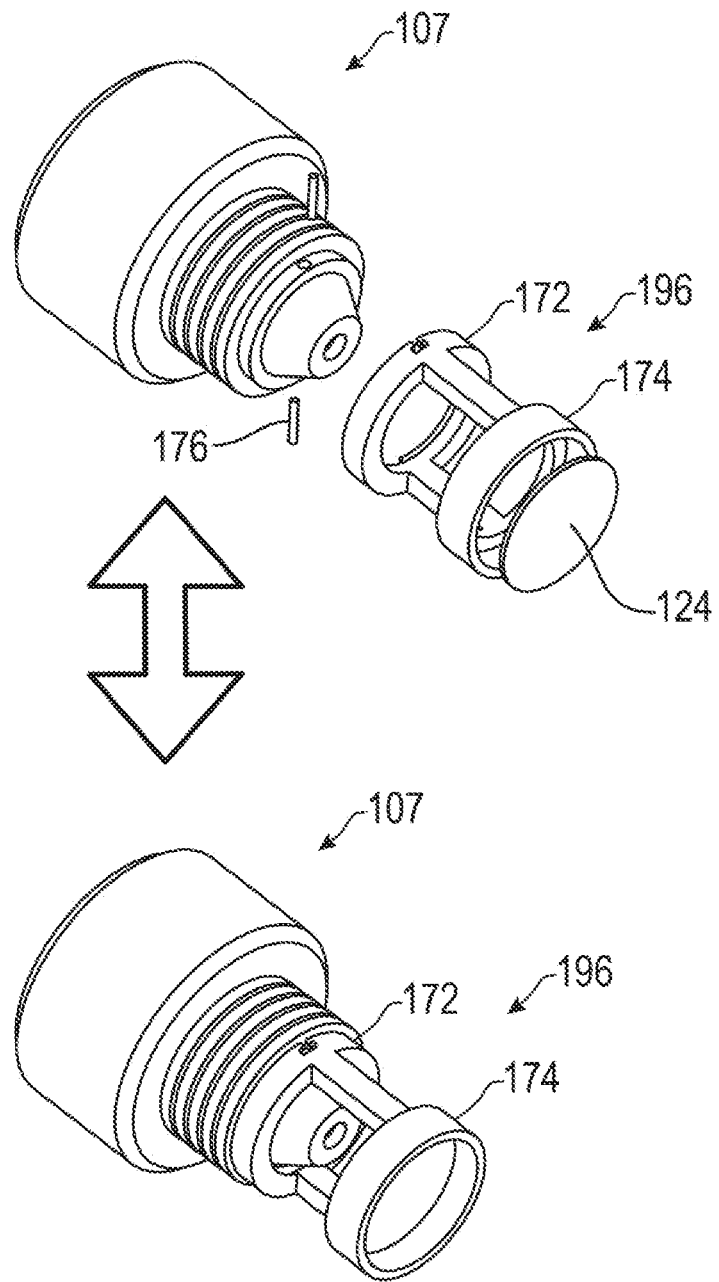
FIG. 21 is an illustration of the nozzle assembly and collection surface holder for the module of FIG. 1.
Figure 22:
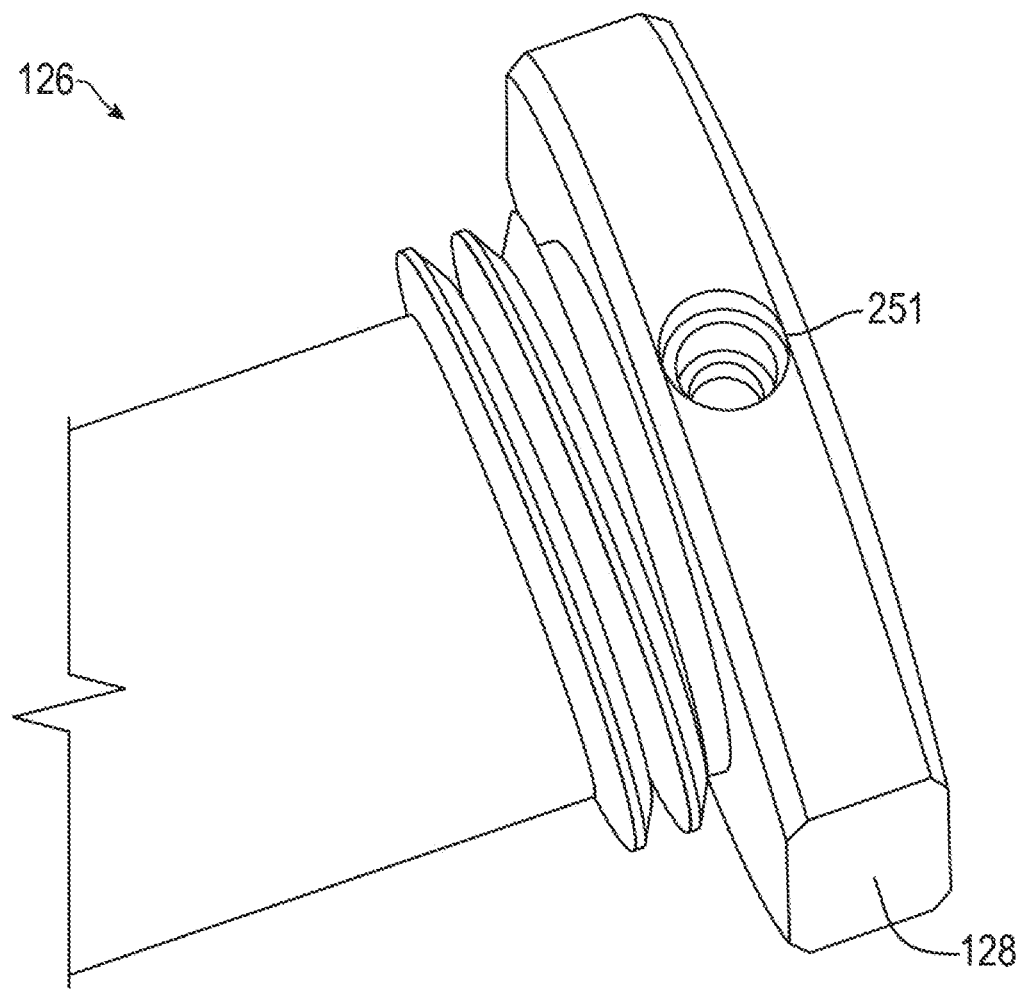
FIG. 22 is a magnified view of a portion of the radiator assembly for the module of FIG. 1.
Figure 23:
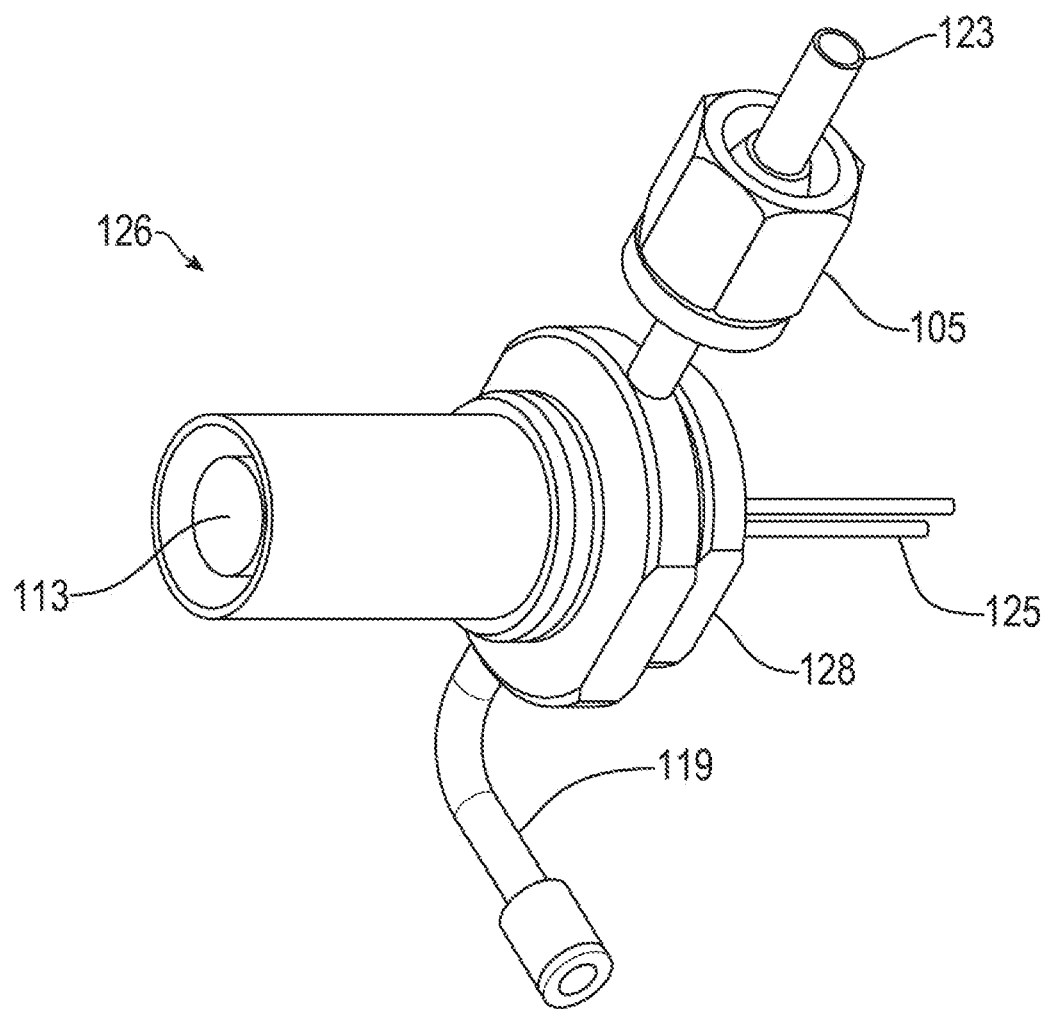
FIGS. 23 and 24 are illustrations of the radiator assembly for the module of FIG. 1.
Figure 24:
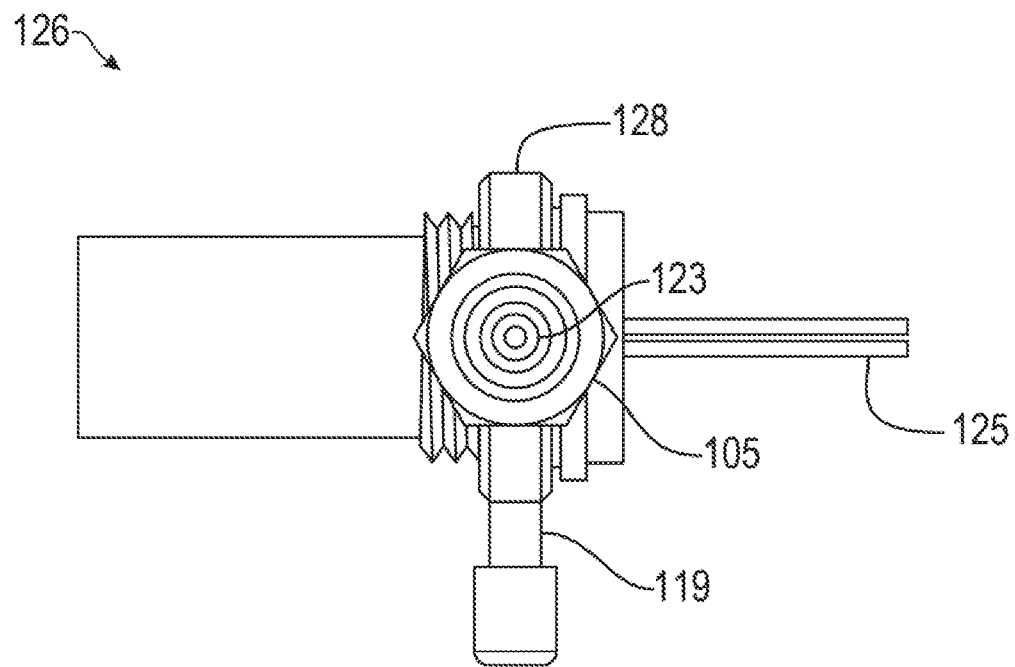
Figure 25:
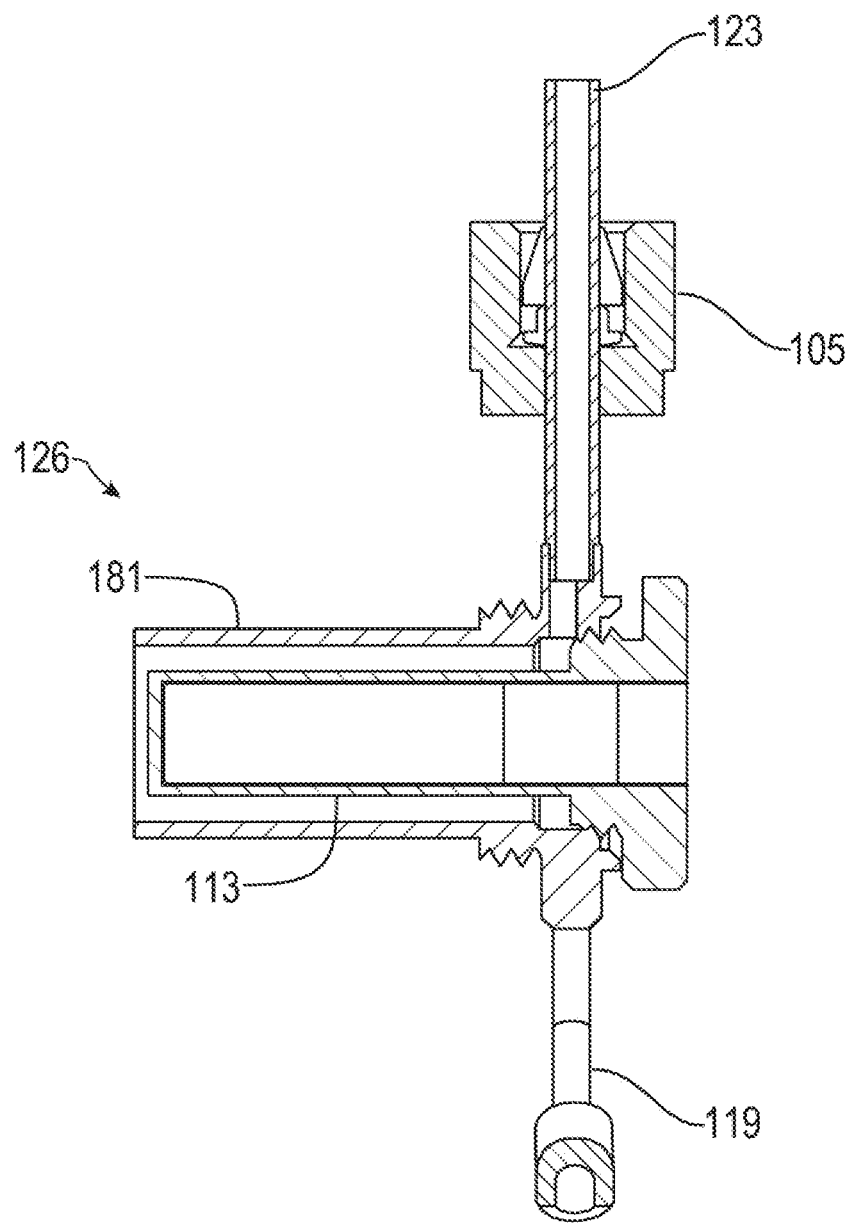
FIG. 25 is a cross-sectional illustration of the radiator assembly for the module of FIG. 1.
Figure 26:
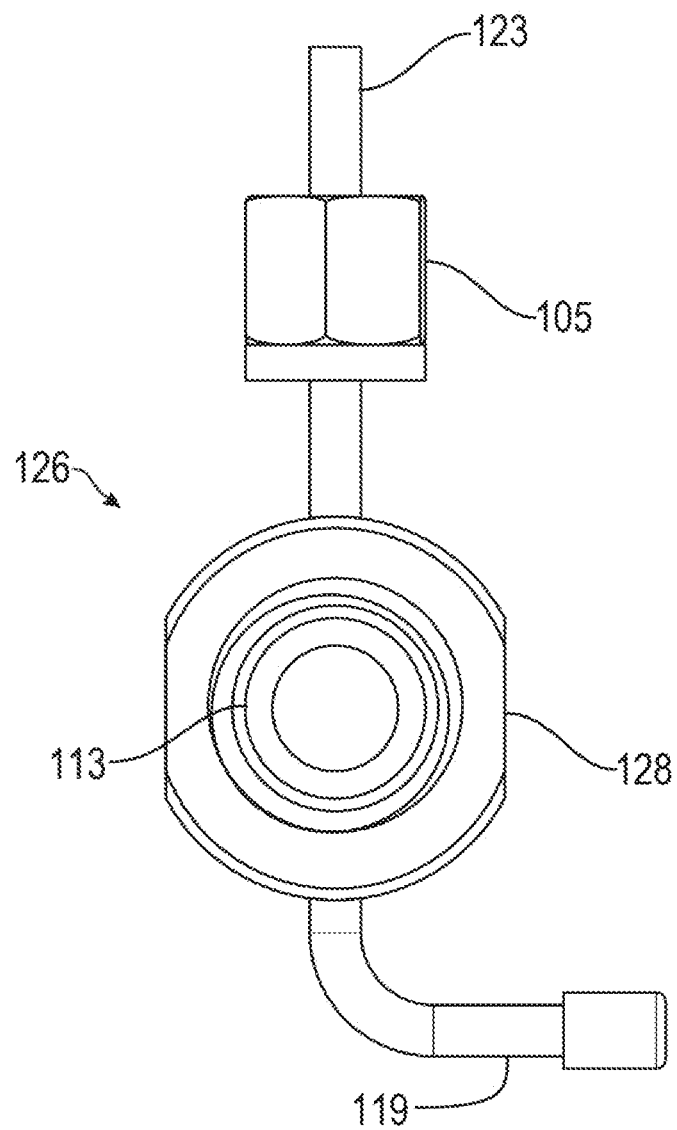
FIG. 26 is an illustration of the radiator assembly for the module of FIG. 1.
Figure 27:
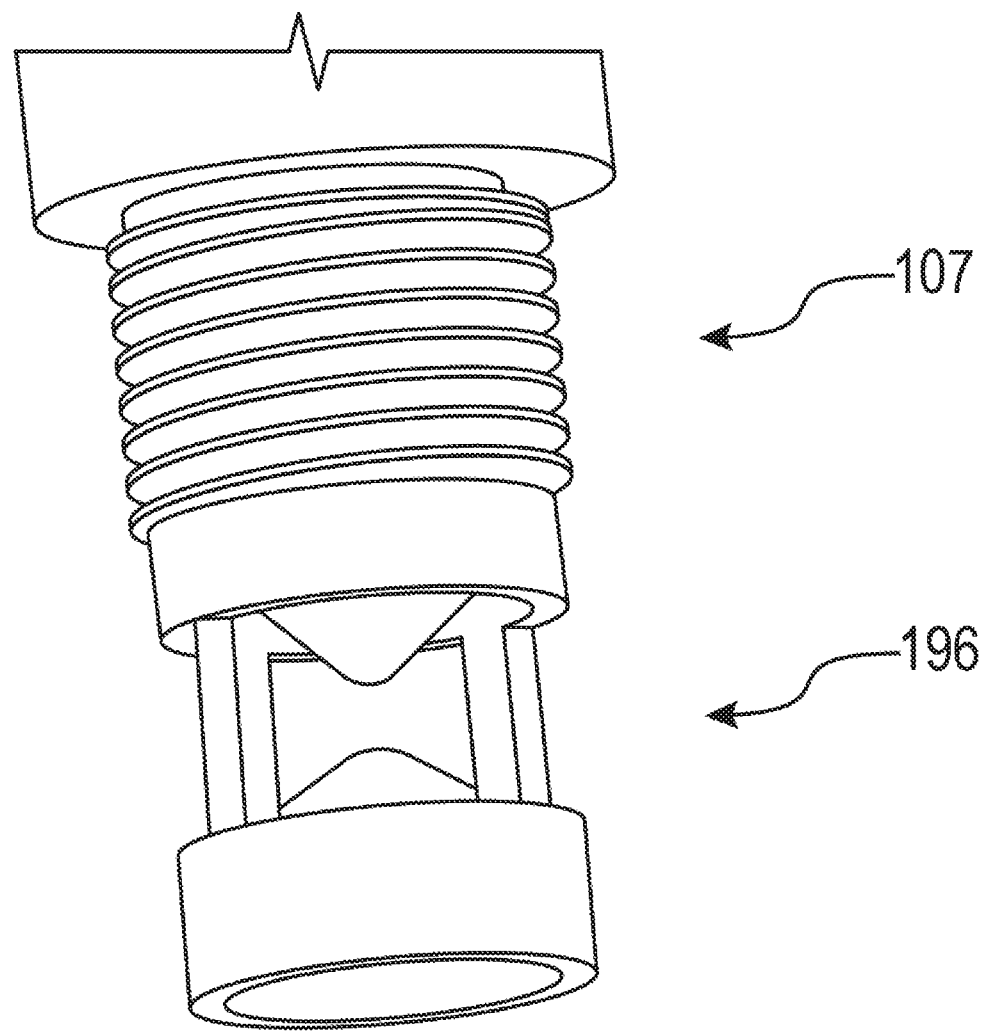
FIG. 27 is an illustration of the nozzle assembly and collection surface holder for the module of FIG. 1.

The collection surface holder 196 is shown in greater detail in FIGS. 21-22. As seen therein, the collection surface holder 196 is an open cylinder having a first annulus 172 that couples with the nozzle assembly, and a second annulus 174 that couples with the collection surface 124. The nozzle assembly 107 may be rotated in a clockwise or counter-clockwise manner to adjust the pressure with which it pressingly engages the collection surface holder 196.

Figure 7:
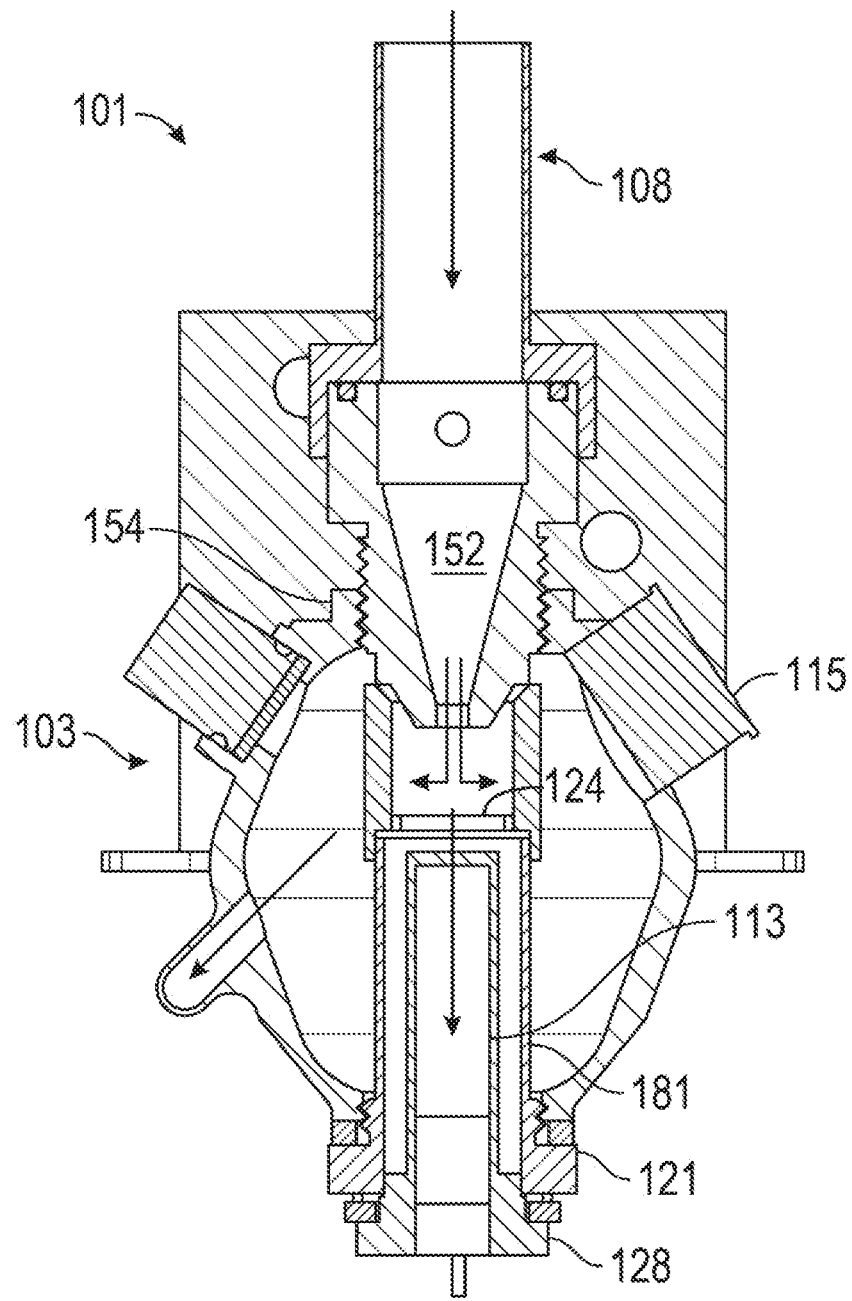
FIG. 7 is a cross-sectional view of the module of FIG. 3.
Figure 8:
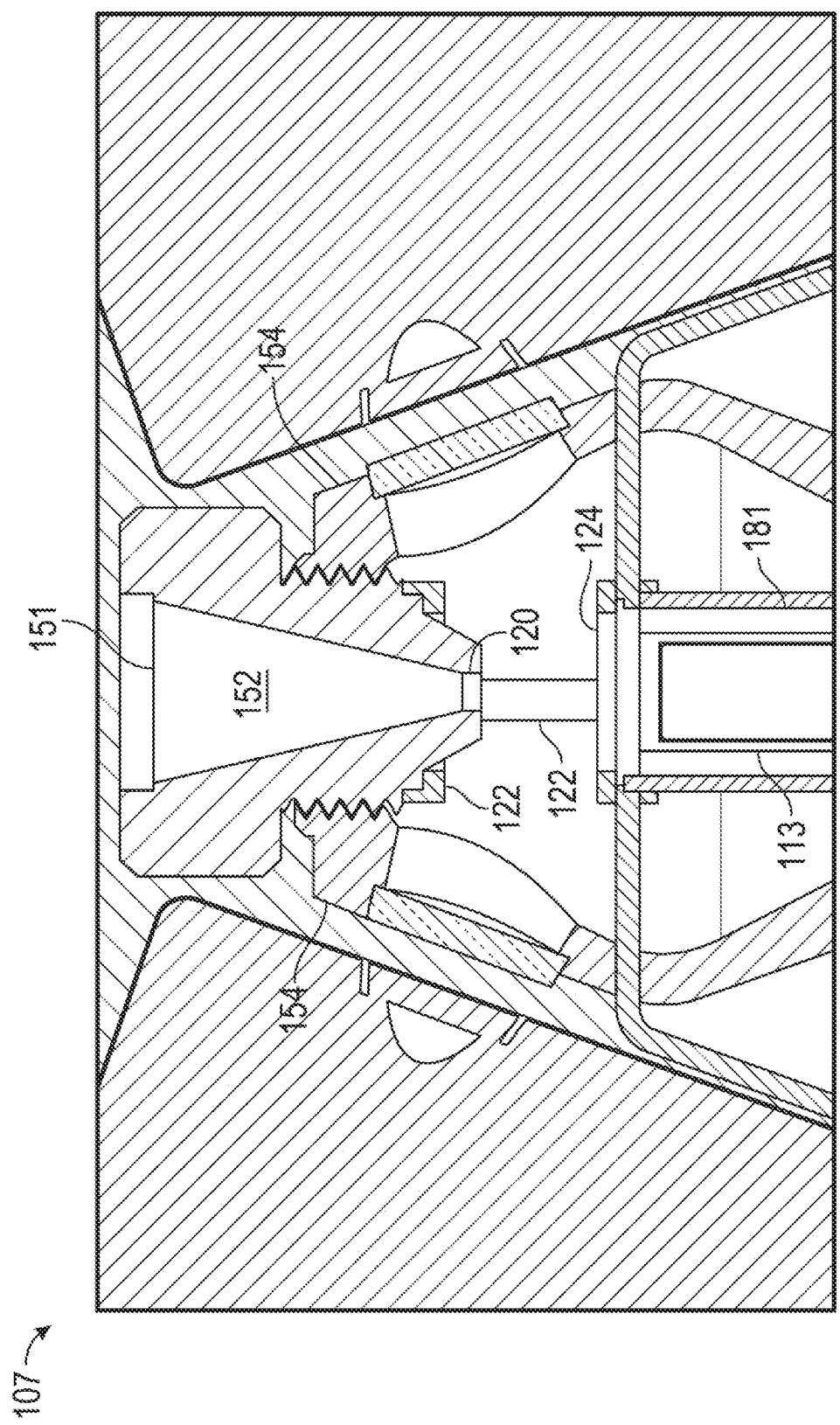
FIG. 8 is a magnified cross-section of a portion of the module of FIG. 1.
Figure 9:
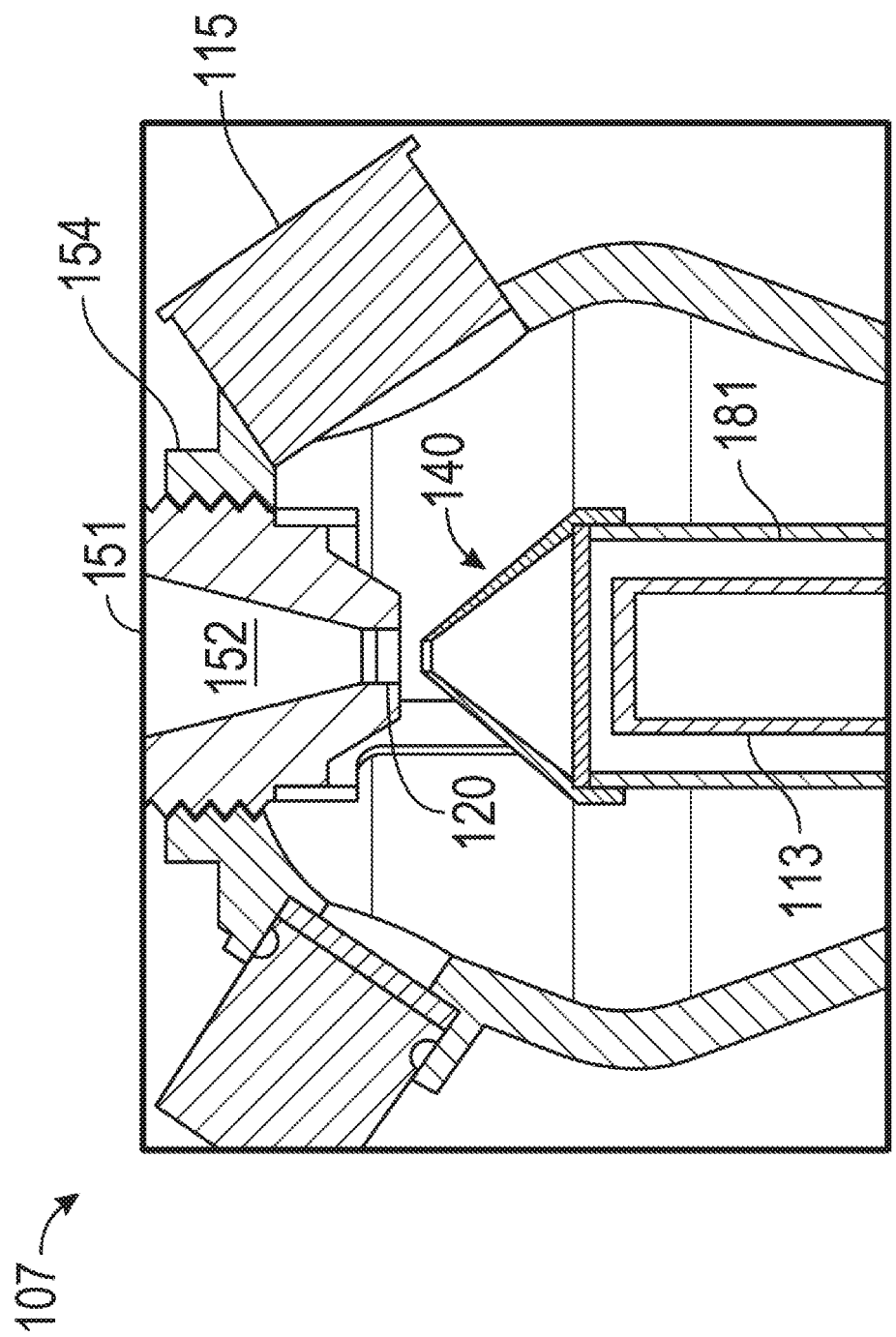
FIG. 9 is a magnified cross-section of a portion of the module of FIG. 1.
Figure 10:
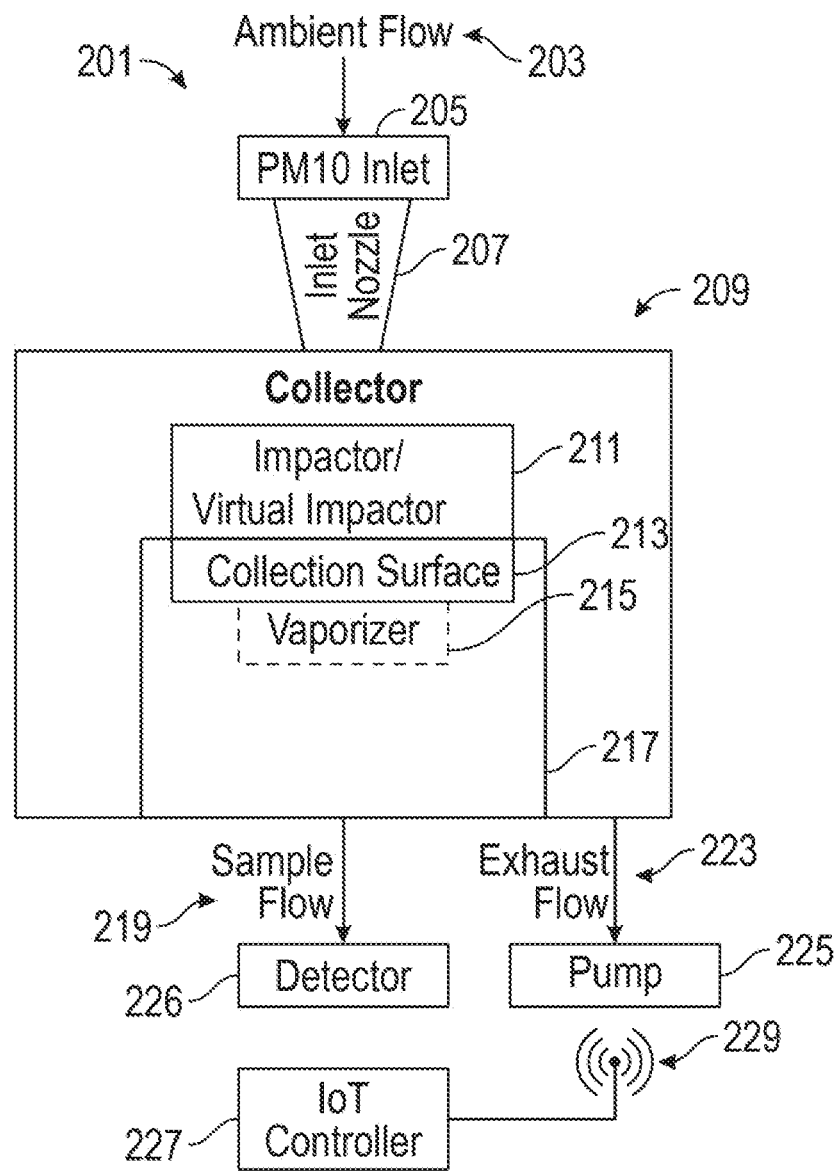
FIG. 10 is an aerosol and enhanced sample module diagram and flow path.
Figure 28:
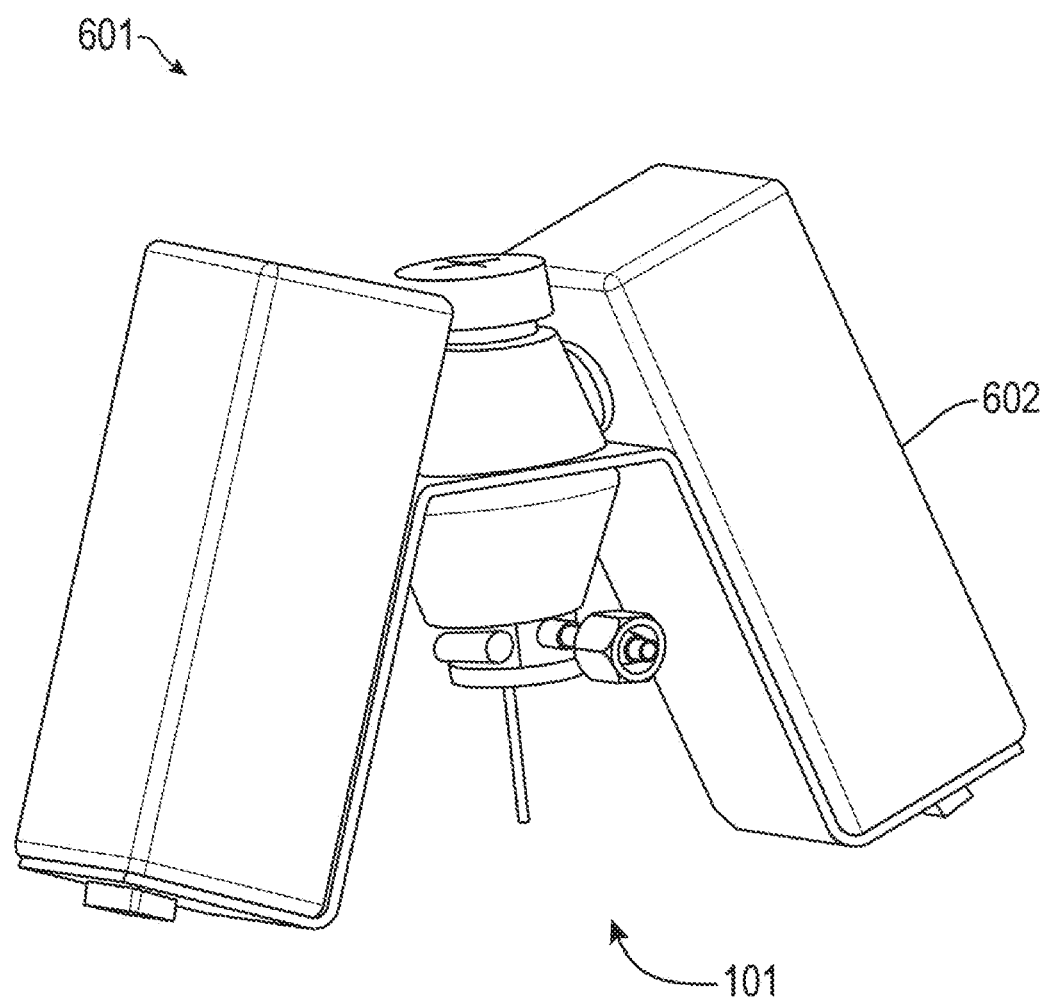
FIG. 28 is an illustration of an embodiment of the module of FIG. 1 equipped with heat lamps.

It will be appreciated that the collection surface holder 196 thus maintains the collection surface in a fixed, spaced-apart orientation with respect to the nozzle orifice 120, and its open construction allows for a major fluidic flow in a direction parallel to the collection surface 124 (see, e.g., the flow arrows in FIG. 7). In the particular embodiment depicted, the collection surface holder 196 is releasably engaged to the nozzle assembly 107 by means of a pin 176, although embodiments are also possible in which the collection surface holder 196 is secured to the nozzle assembly 107 in other manners. For example, embodiments are possible in which the collection surface holder 196 is press fit onto the nozzle assembly 107 (see FIG. 28).

In a preferred embodiment, the interior structure of the housing 103 creates a major fluidic flow parallel to the collection surface 124 and a minor fluidic flow which preferably flows through the collection surface 124 (although embodiments are also possible where, for example, the minor fluidic flow passes through apertures or channels immediately adjacent to the collection surface 124). This operation causes airborne particulate materials to accumulate on the collection surface 124. The accumulated particulate materials may then be subject to suitable analysis, preferably by vaporizing them, and then drawing the vaporized materials through the minor exhaust line 123 for suitable analysis. Such analysis may include, for example, mass spectrometry, ion mobility spectrometry, differential mobility spectrometry, field asymmetric ion mobility spectrometry, infrared spectroscopy, Fourier transform infrared spectroscopy, or Raman spectroscopy. In the particular embodiment depicted, the minor exhaust line 123 is equipped with a suitable coupler 105, such as a Swagelok nut, to allow it to be coupled to various detectors, sensors or other instruments for the foregoing purposes.

The manner in which the vaporized materials are passed from the collection surface 124 to the minor exhaust line 123 may be appreciated with respect to FIGS. 6-10. In particular, the aerosol and vapor enhanced sample module 101 is equipped with a radiator assembly 126 which is equipped with a heating cartridge 113 and which is screwed into a threaded orifice on the bottom of the aerosol and vapor enhanced sample module 101. The collection surface holder 196 sits upon the radiator assembly 126, and is equipped with a gas transport region 181. Vaporized materials pass through (or in some embodiments, around) the collection surface 124 and enter the gas transport region 181. From there, they pass through an orifice 251 (see FIG. 22) in the radiator assembly 126 and into the minor exhaust line 123. The connection between the radiator assembly 126 and the minor exhaust line 123 may be further appreciated with respect to FIG. 20 and FIGS. 23-26.

Figure 3:
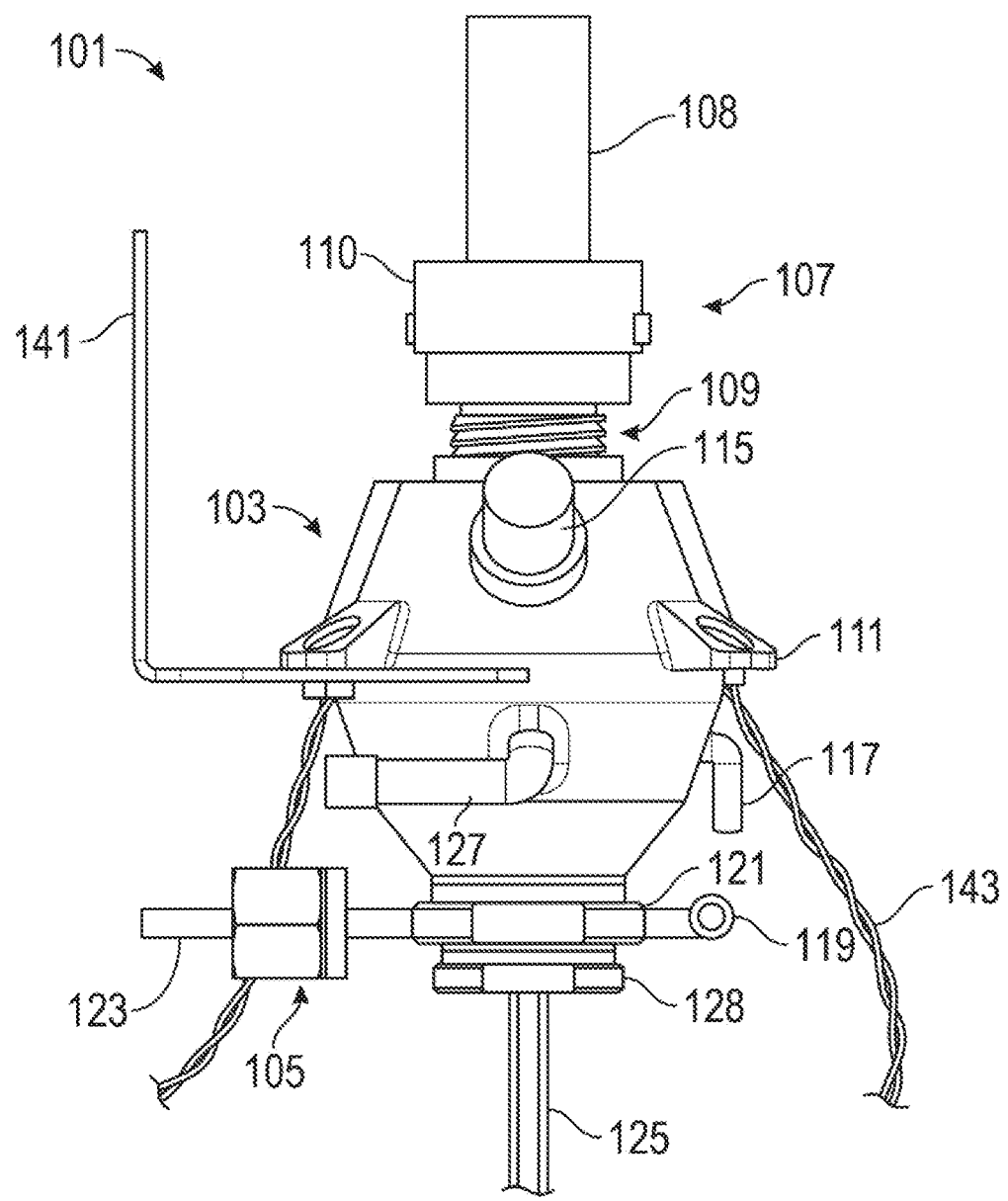
FIG. 3 is an illustration of the aerosol and enhanced sample module of FIG. 1 shown with a mounting bracket, electrical wires, a conduit and an adapter for connecting the nozzle assembly to the conduit.
Figure 4:
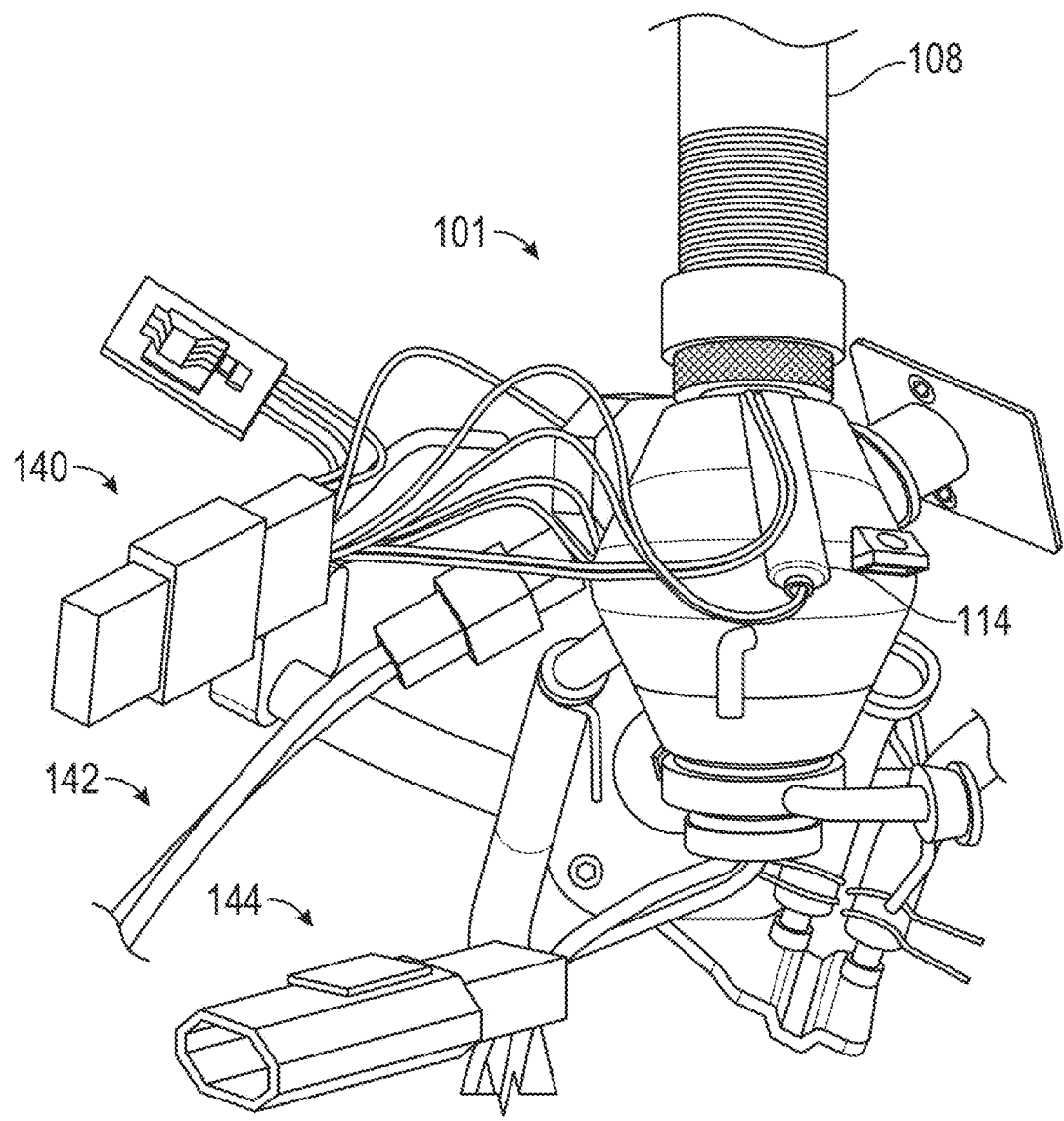
FIG. 4 is an illustration of the aerosol and enhanced sample module of FIG. 1 shown interfaces with various external devices.

Referring again to FIGS. 1-2, the housing 103 is equipped with a plurality of integrated mounts 111 that allow the aerosol and vapor enhanced sample module 101 to be mounted on, or attached to, a suitable substrate. The aerosol and vapor enhanced sample module 101 may be mounted directly to a substrate or, as seen in FIG. 3, it may be mounted on a bracket 141 or other suitable support structure. aerosol and vapor enhanced sample module 101 may also be mounted on a remote sampling conduit 108 as depicted in FIG. 4, in which case the conduit 108 will typically be in fluidic communication with the ambient environment or with another environment to be sampled. The remote sampling conduit 108 may also be attached to an aerosol/vapor generation system for testing purposes. As seen in FIG. 3, the nozzle assembly 107 may be equipped with a quick connect 110 to allow a user to quickly couple (and decouple) the nozzle assembly 107 to a remote sampling conduit 108.

The housing 103 is further equipped with a tap-off port 117. The tap-off port 117 may be utilized, for example, to measure the pressure drop across the inlet nozzle assembly 107 from ambient pressure. The optimal value for this pressure drop $\Delta P_1$ may depend on various factors such as, for example, on the configuration of the device, its intended use, and the desired flow rate. However, the pressure drop is typically less than 100 mbar. Thus, for example, at a flow rate of 6 L/min, $\Delta P_1$ is preferably about 10-20 mbar. However, with increased flows of 10 L/min and a lower cutpoint, pressure drops may be closer to 60 mbar. Port 119 may be utilized, for example, to measure the pressure drop $\Delta P_2$ across the collection surface 124 from the bottom of the housing 103 (which is in fluidic communication with port 119).

Figure 29:
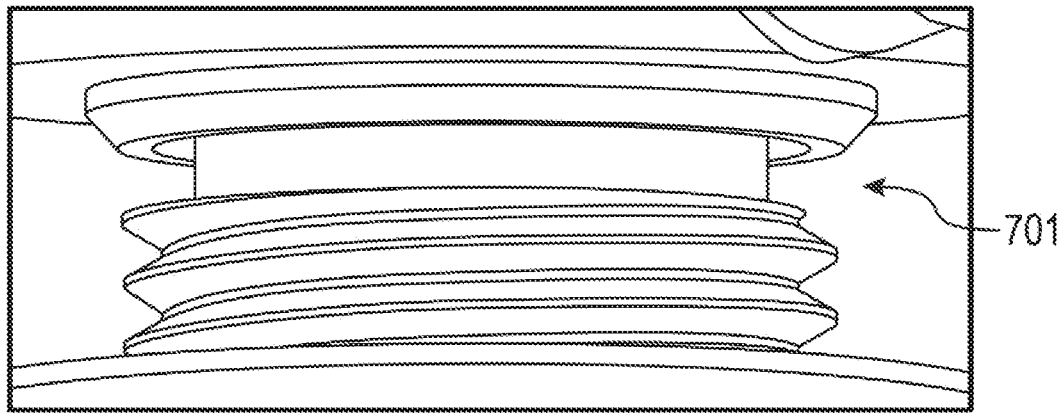
FIG. 29 is an illustration of a particular, non-limiting embodiment of the use of thermal breaks to minimize heat transfer from the radiator assembly to the chamber in the module of FIG. 1.

The housing 103 is also equipped with an access/mounting port 113 for an IR heating element. Such an element may be utilized, for example, as a sole or additional means to heat the collection surface 124. An example of such an embodiment 601 is depicted in FIG. 29, which shows the aerosol and vapor enhanced sample module 101 of FIG. 1 equipped with a set of flash lamps 602 for surface heating or bulk particle measurement.

The housing 103 is further equipped with a receiver port 115. Various sensors may be installed on the receiver port 115 for various purposes. Fort example, a surface temperature thermocouple or IR temperature measurement sensor may be installed in the receiver port 115 to determine the temperature of the collection surface 124. As seen in FIG. 5, an optional thermocouple electrical conduit 195 is also provided in the radiator assembly 126 to allow a thermocouple to directly contact the bottom of the collection surface 124).

In some applications, the receiver port 115 may be utilized to mount chemical analytical instruments on the housing, although it is preferred that such instruments are attached to the minor exhaust line 123.

The opposing end of the housing from the threaded aperture 154 (see FIG. 5) is equipped with a radiator assembly 126. The radiator assembly 126 may be utilized to heat the collection surface 124, and is equipped with a power cord 125 for that purpose. To a similar end, and as best seen in FIG. 4, the housing 103 is further equipped with integrated receiving tubes 114 for conductive heating elements.

As shown in FIG. 4, the aerosol and vapor enhanced sample module 101 may be connected to various external devices. In the particular embodiment shown, these include chamber heaters and thermistors 140, a collection surface temperature sensor 142 and a main radiator (conductive heater power) and thermocouple return 144.

With reference to FIG. 6, the minor flow path inside the aerosol and vapor enhanced sample module 101 is depicted with arrows. As seen therein, the minor flow path extends from the collection surface 124 and into the sampling tube 181, where it is heated and transferred to the minor exhaust line 123 for analysis. Port 127 is used typically for a pressure measurement port. The arrow 268 represents an airflow that allows a low differential pressure within the aerosol and vapor enhanced sample module 101, thus eliminating the need for high pressure drop detector pumps.

With reference to FIG. 7, the major flow path inside the aerosol and vapor enhanced sample module 101 is depicted with arrows. As seen therein, the minor flow path extends from conduit 108 through the nozzle assembly 107, and exits through the major exhaust line 127. As noted above, the minor flow enters the sampling tube 181.

With reference to FIG. 8, a magnified view of the nozzle assembly 107 is depicted in cross-section. As seen therein, the nozzle assembly is recessed further into the housing 103, thus reducing the overall separation between the orifice 120 and the collection surface 124.

FIG. 9 is a magnified view of the nozzle assembly 107 is depicted in cross-section, with a virtual impactor 140 installed. The virtual impactor 140 is connected to the collection surface holder 196 (see FIG. 22), with only one leg of the collection surface holder 196 visible.

The aerosol and vapor enhanced sample module 101 depicted in FIG. 1 incorporates a flexible design to facilitate rapid integration into a variety of detection platforms. Notable features of this system include the collection of particles combined with several modes of desorption/vaporization, including optical and thermal modes up to temperatures of 650° C. with low power requirements. Advantageously, 3-D metal printing techniques may be utilized in the fabrication of components of the aerosol and vapor enhanced sample module to facilitate rapid customization to a variety of chemical detection platforms. In addition, by incorporating multiple input and output connections coupled with current controller technologies, the aerosol and vapor enhanced sample module 101 may be readily adapted for use in various detection and sampling systems.

The flow path of an aerosol and vapor enhanced sample module of the type disclosed herein may be appreciated with respect to the particular, non-limiting embodiment depicted in FIG. 10. As seen therein, the depicted flow path 201 extends from the ambient environment 203 through an inlet 205 and nozzle 207, and into a collector 209. From there, the flow path is divided into a first, major flow which exits the collector 209 under the influence of a pump 225 as an exhaust flow 223, and a second, minor flow which passes through a cut-point filter 211, a concentrator 213 and a vaporizer 215 into a sampler 217. A sample flow 219 from the sampler 217 passes through a detector 221, where it is subjected to suitable analysis. The operation of the device, including the flow rates through the device, is controlled by an IoT controller 227, which communicates via suitable wireless communications 229 and protocols to other devices.

FIG. 11 depicts a screen shot of the Sample Module Controller for a particular, non-limiting embodiment of such software. As seen therein, the Sample Module Controller 301 in this particular embodiment provides a user interface that enables a user to control and/or monitor various features and operating parameters of the aerosol and vapor enhanced sample module converter. These include fields for allowing the user to enter or adjust the screen (collection surface) setpoint (in ° C.), housing setpoint (in ° C.), pressure setpoint (in mBar), flash on time (in seconds), collect time (in seconds), and test pump duration (in seconds). Selectable options are also provided to enable the user to test a lamp in the device, select an operational mode (e.g., continuous or pulsed), enabling logging (for example, for troubleshooting purposes), and to connect or disconnect the device from WiFi communications.

The Sample Module Controller 301 also displays the current value or status of various operational parameters. These include, for example, an indication of whether the flash, pump, screen (collection surface) heater, and housing heater are on or off, the response status of the device, and the current number of packets. The Sample Module Controller 301 also displays the fault status of the flash, screen (collection surface) temperature, screen (collection surface) heat, pump, nozzle, filter and flow. The Sample Module Controller 301 further displays the current value of the screen (collection surface) temperature (in ° C.), the housing temperature (in ° C.), the filter pressure (in mBar), and the nozzle pressure (in mBar).

Figure 12:
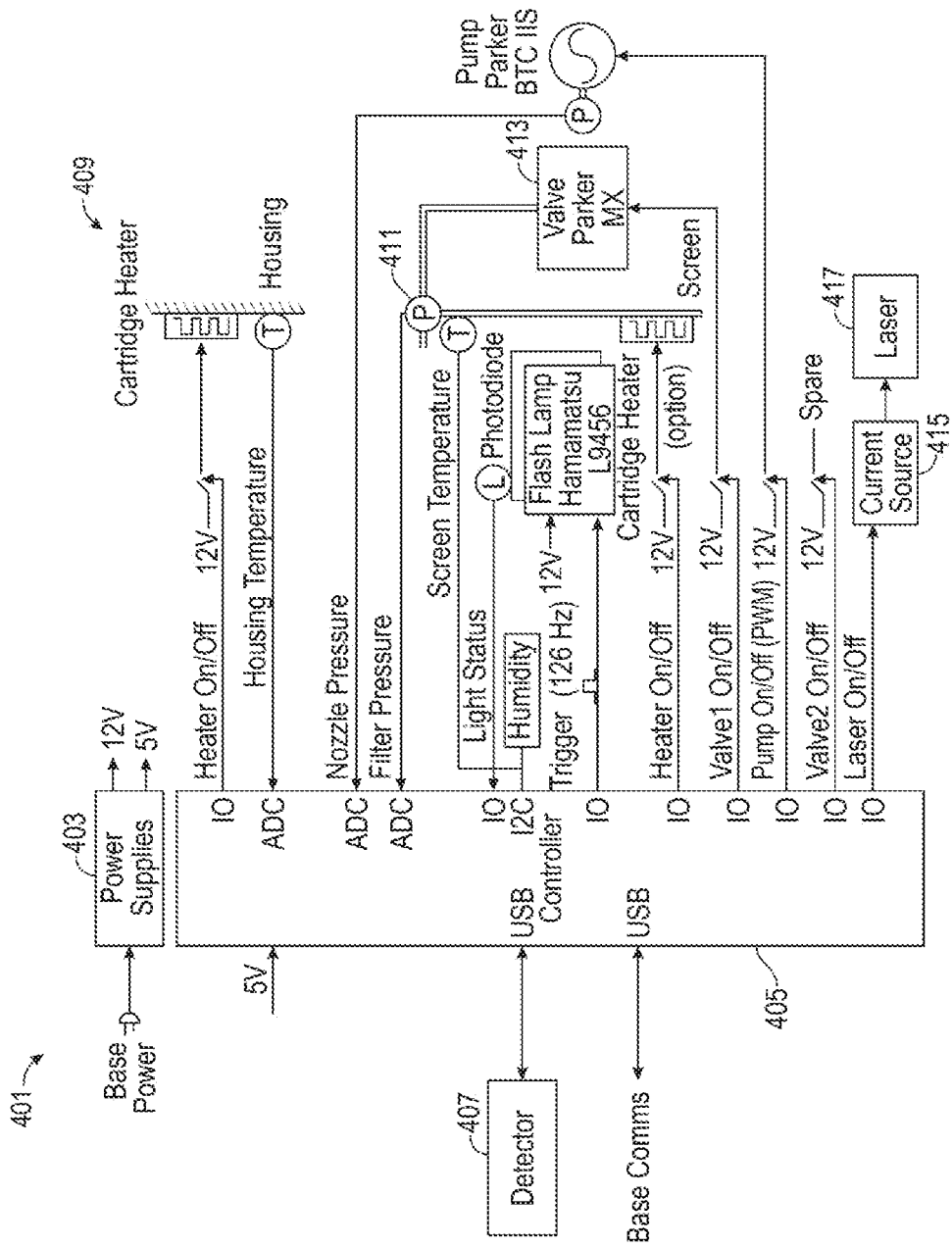
FIG. 12 is a diagram of an electrical system for an aerosol and enhanced sample module.

FIG. 12 depicts a particular, non-limiting embodiment of the electrical configuration of the aerosol and vapor enhanced sample module 101 depicted in FIG. 1. As seen therein, the aerosol and vapor enhanced sample module 101 is equipped with suitable circuitry 401 to enable the various components of the system to interoperate to perform the various functions of the system. This circuitry powers the device and enables it to communicate to external devices. These components include the power supplies 403, USB controller 405, detectors 407, heaters 409, pumps 411, valves 413, current source 415 and lasers 417. Some examples of the functionalities performed by these components include monitoring nozzle and filter pressures, turning pumps and valves on and off, and monitoring the temperature of the collection surface.

Figure 13:
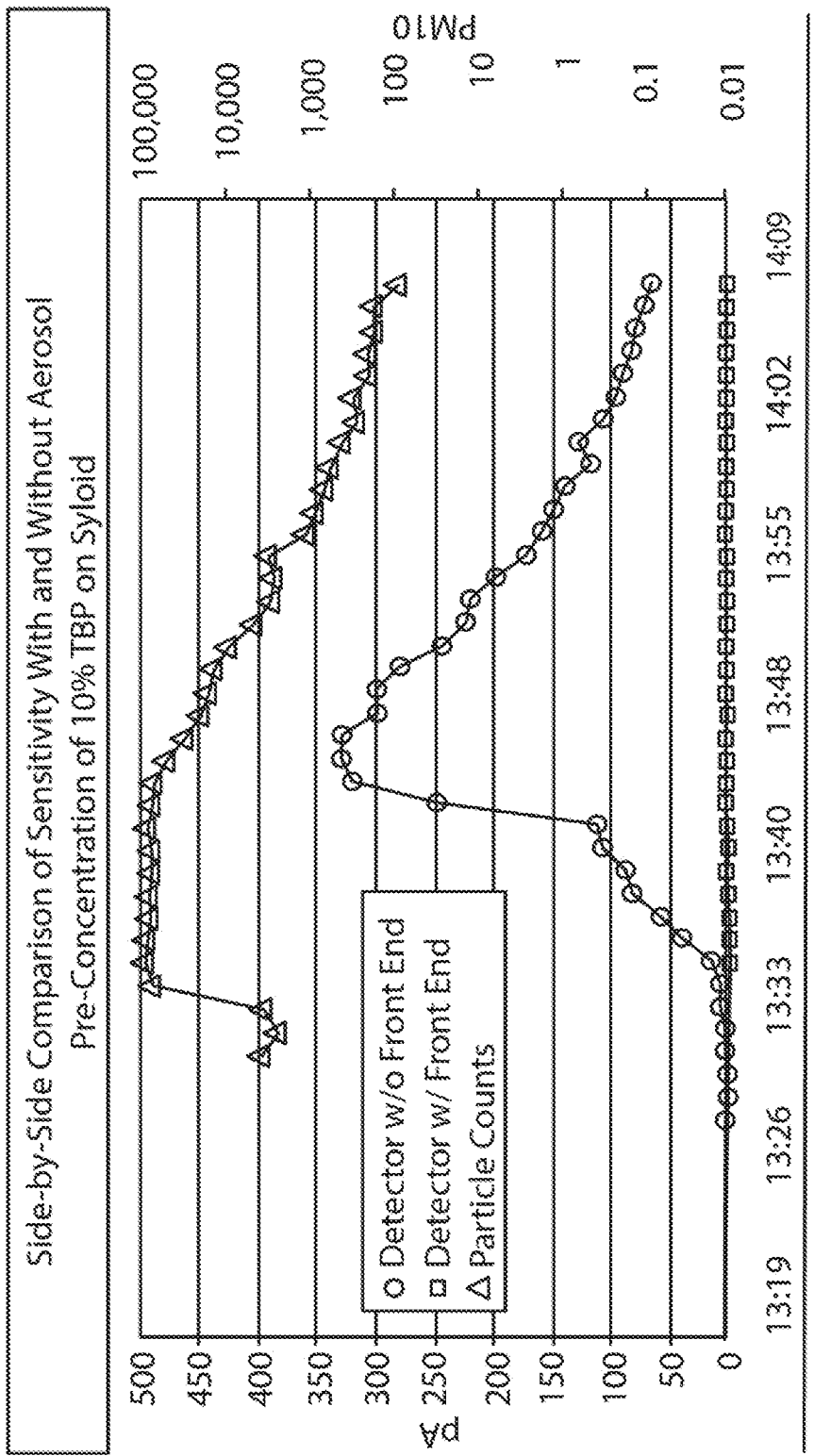
FIG. 13 is a series of graphs based on data collected with a system of the type disclosed herein. The graphs depict caffeine desorbed off of 5 µm syloid particles.

FIG. 13 is a graph of data obtained from a COTS (commercial off-the-shelf) detector connected (with a front end) to the output of the aerosol and vapor enhanced sample module, and referenced particle count data. The detector concentration rise is nearly real-time with the particle concentration increase, with a slight delay as the material enters, is collected, concentrated, vaporized and passed to the detector. There is also a comparison without the aerosol and vapor enhanced sample module (without the front end) demonstrating that the ambient concentration is below the detection sensitivity for this device.

The graph provides a side-by-side comparison of sensitivity with and without aerosol pre-concentration of 10% TBP on Syloid. The detector with the front end signal is 325 pA above the baseline. The detector without the front end signal is 1.75 pA above the baseline. The concentration factor $C_F$ is given by EQUATION 1 below:

$$C_F = \frac{S_{SM} - B}{S_{VM} - B} \quad \text{(EQUATION 1)}$$

where $S_{SM}$ is the SM signal, $S_{VM}$ is the VM signal and B is the baseline.

Figure 14:
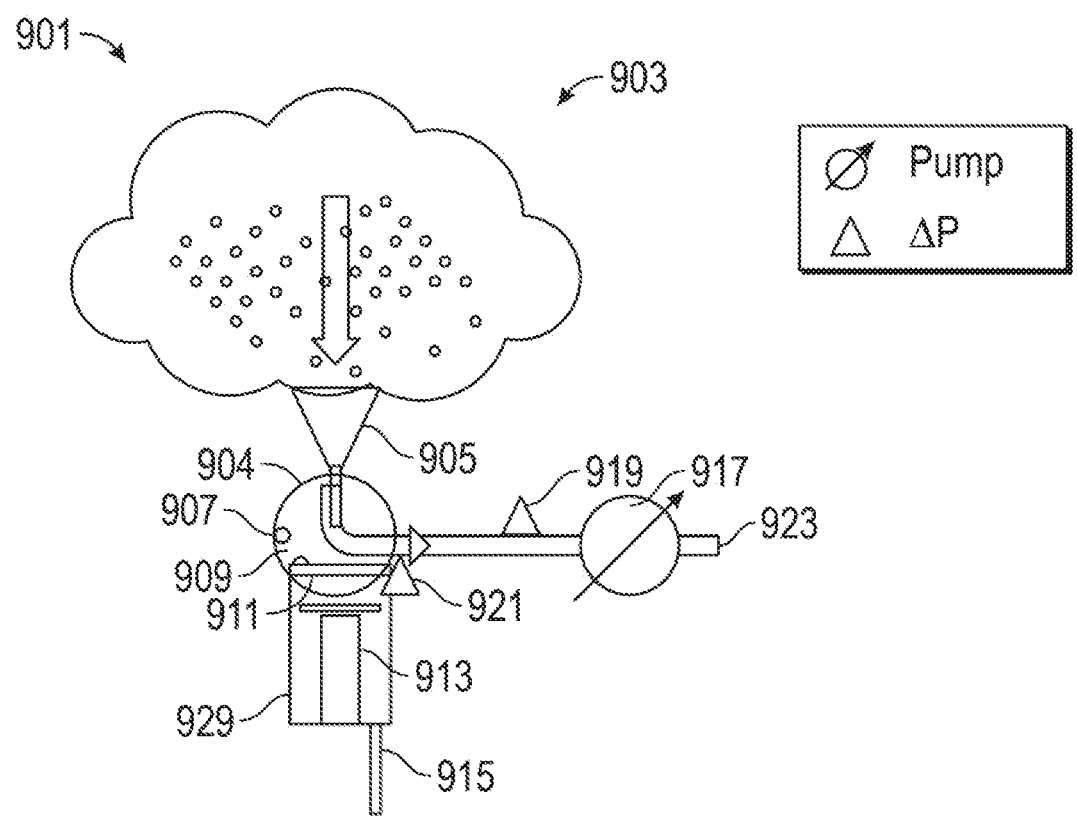
FIG. 14 is a particular, non-limiting illustration of the use of an aerosol and vapor enhanced sample module disclosed herein.
Figure 15:
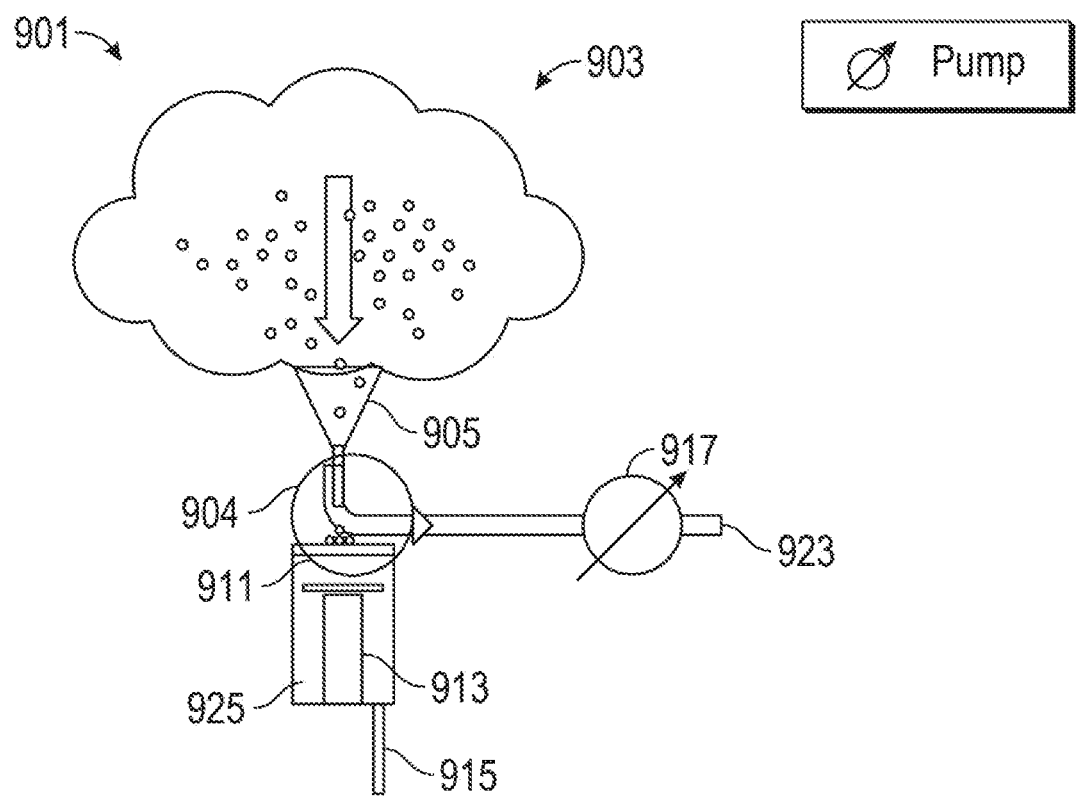
FIG. 15 depicts the module of FIG. 14 after sample accumulation.

FIG. 14 is a particular, non-limiting illustration of the use of an aerosol and vapor enhanced sample module disclosed herein. As seen therein, the system 901 is exposed to a particle-laden cloud 903 that the system is to sample. The system includes a, inlet region 905 and a chamber envelope 904. A pressure sensor 919 is provided to monitor the pressure drop across the inlet nozzle, and a temperature probe 907 is provided to monitor the chamber temperature. A collection surface 911 is provided upon which collected particulate matter accumulates. The system 901 is further equipped with a pump 917, a pump exhaust 923, a differential pressure monitor 921 which monitors the pressure across the collection surface 911, a radiator assembly 913, a sampling tube 929, and a minor flow sample transfer tube 915 which is attached to a detector, sensor or sampler (not shown). FIG. 15 depicts the system 901 of FIG. 14 after sample accumulation.

Figure 16:
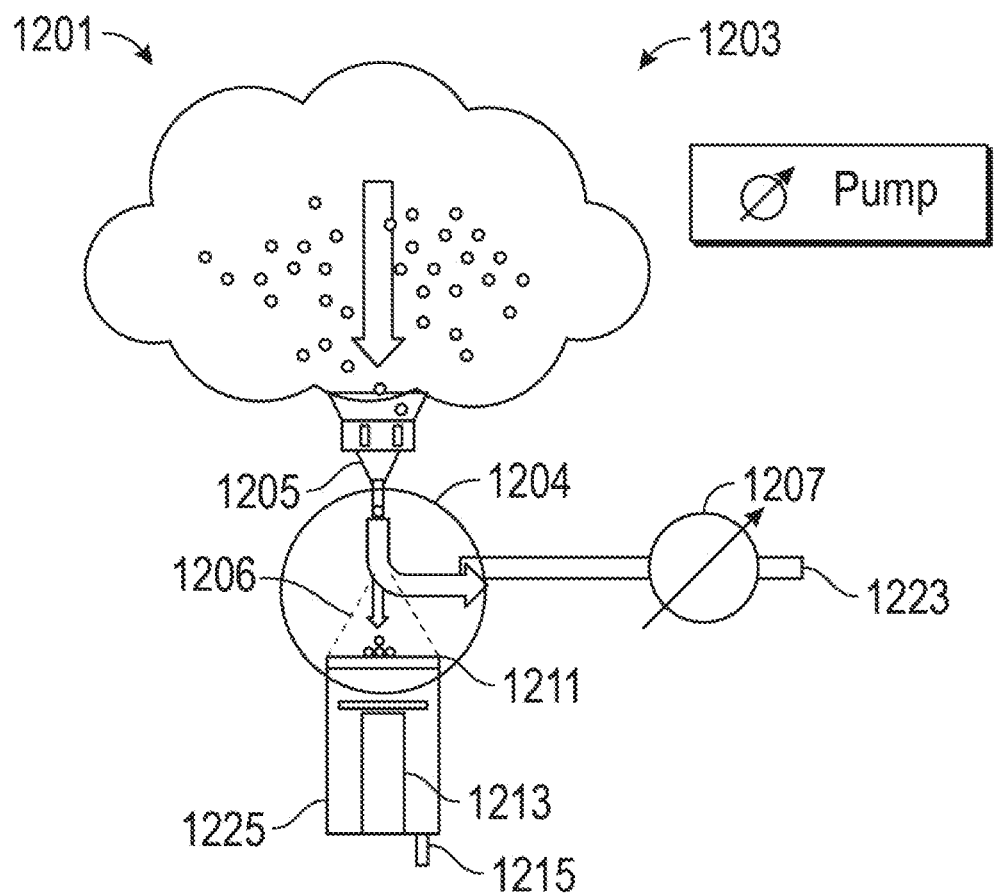
FIG. 16 is a variation of the system of FIG. 15 equipped with a virtual impaction cone.
Figure 17:
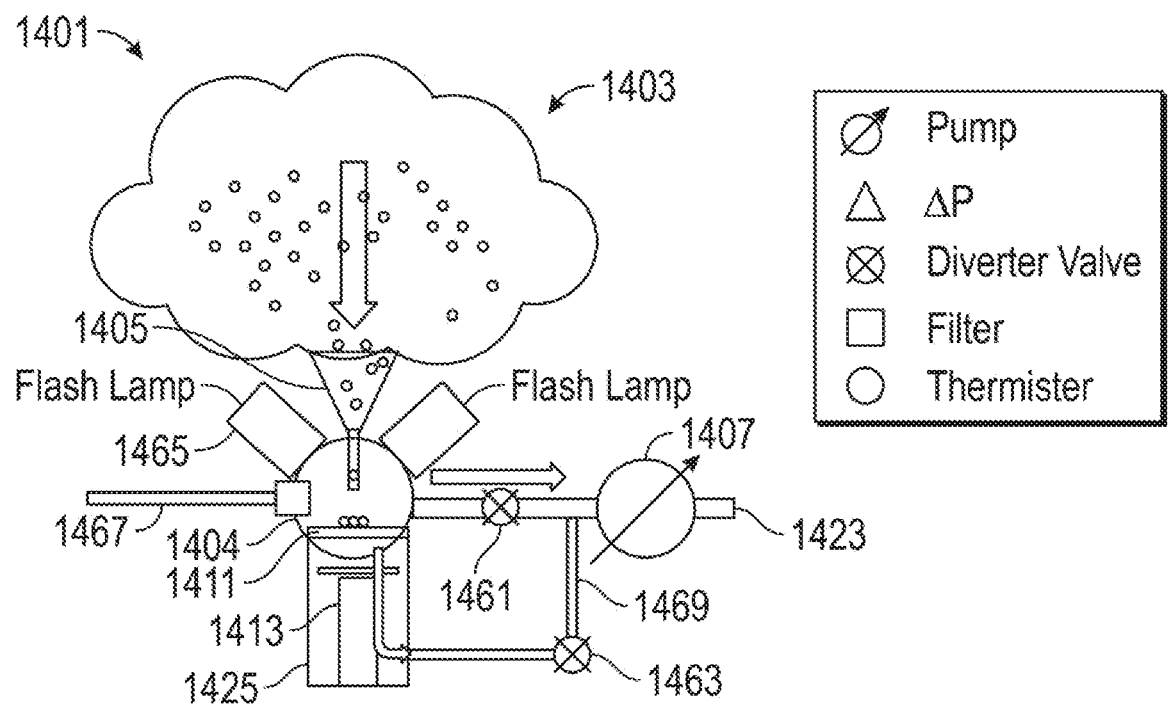
FIG. 17 is an illustration of an aerosol and vapor enhanced sample module which is similar to the module of FIG. 15, but which is equipped with additional connections such that the chamber volume can be used to generate a pulsed, large volume of gas to accommodate a sensor with a long sample time requirement.

FIG. 16 is a variation of the system of FIG. 15 equipped with a virtual impaction cone 1206. As seen therein, the system 1201 is exposed to a particle-laden cloud 1203 that the system is to sample. The system includes a, inlet region 1205 and a chamber envelope 1204. A pressure sensor 1219 is provided to monitor the pressure drop across the inlet nozzle, and a temperature probe 1207 is provided to monitor the chamber temperature. A collection surface 1211 is provided upon which collected particulate matter accumulates. The system 1201 is further equipped with a pump 1217, a pump exhaust 1223, a differential pressure monitor 1221 which monitors the pressure across the collection surface 1211, a radiator assembly 1213, a sampling tube 1229, and a minor flow sample transfer tube 1215 which is attached to a detector, sensor or sampler (not shown). FIG. 17 depicts the system 1201 after particles have landed on the collection surface 1211 via the virtual impaction cone 1206.

FIG. 17 is an illustration of an aerosol and vapor enhanced sample module 1401 which is similar to that of FIG. 15, but which is equipped with additional connections such that the chamber volume can be used to generate a pulsed, large volume of gas to accommodate a sensor with a long sample time requirement. In this embodiment, a multitude of valves 1407, 1461 and 1463 allow for a concentration step, and then sealing of the chamber exhaust points 1423, 1469 during a desorption step using the radiator assembly 1413 and/or optical heating method (as indicated by flash lamps 1465). The resultant vapor fills the sample chamber, where it can then be sampled by the sample transfer tube 1467. In this case, the chamber sample volume is designed to allow a stable or sufficient concentration for the detector flow rate and minimum detection time requirements.

Figure 18:
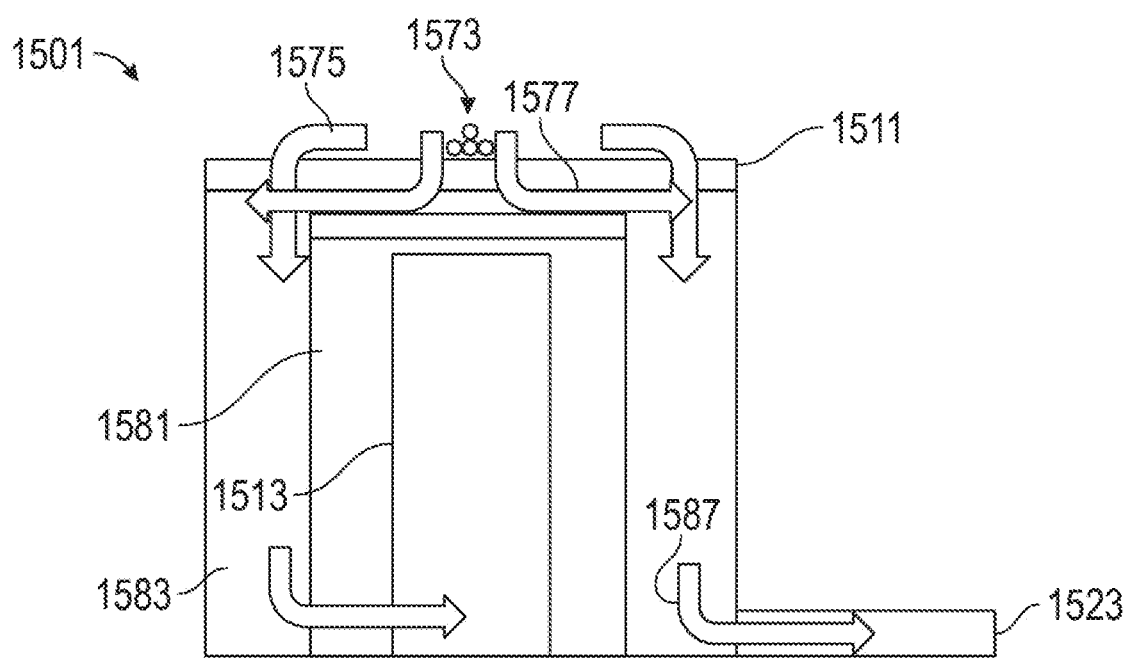
FIG. 18 is an illustration of a particular, non-limiting embodiment of the resultant vapor flow path for an impactor design as the sample is desorbed.

FIG. 18 is an illustration of a particular, non-limiting embodiment of the resultant vapor flow path for an impactor design as the sample 1573 is desorbed. The resultant vapors pass either through (in the case of a screen-like collection surface) or around (in the case of annular rings) the collection surface 1511, past the radiator assembly 1581 and out the sampling transfer tube 1523.

Figure 19:
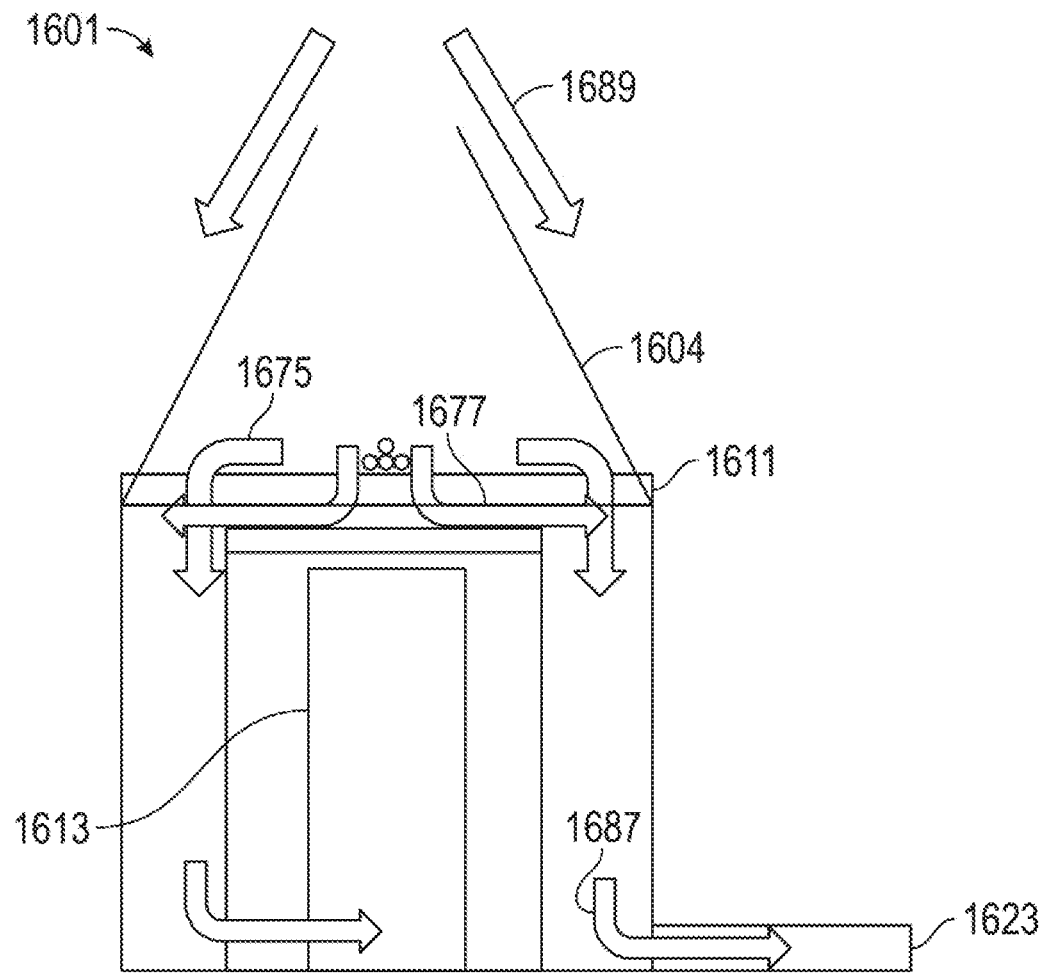
FIG. 19 is an illustration of the resultant vapor flow path for a virtual impactor design where the impactor cone allows the collection of particles on the collection surface and the flow path.
Figure 20:
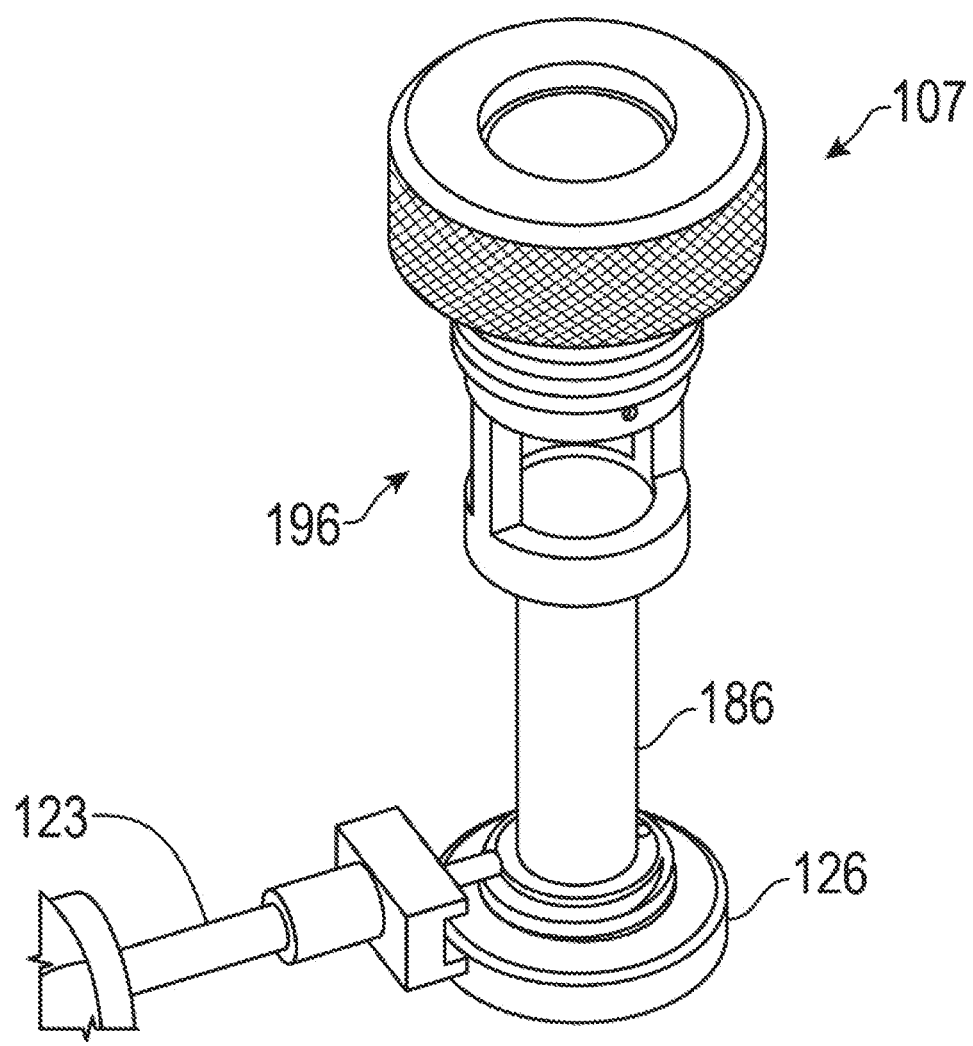
FIG. 20 is an illustration of the nozzle assembly, collection surface holder and radiator assembly for the module of FIG. 1.

FIG. 19 is an illustration of the resultant vapor flow path for a virtual impactor design where the impactor cone 1604 allows the collection of particles on the collection surface and the flow path. The remaining flow path is identical to the embodiment of FIG. 19.

FIG. 29 is an illustration of a particular, non-limiting embodiment of the use of thermal breaks 701 to minimize heat transfer from the radiator assembly to the chamber (see, e.g., FIG. 7). Such thermal breaks may be utilized, for example, in a system of the type depicted in FIG. 7 to provide more effective heating at lower energy consumption as compared to high thermal conductance embodiments.

Figure 30:
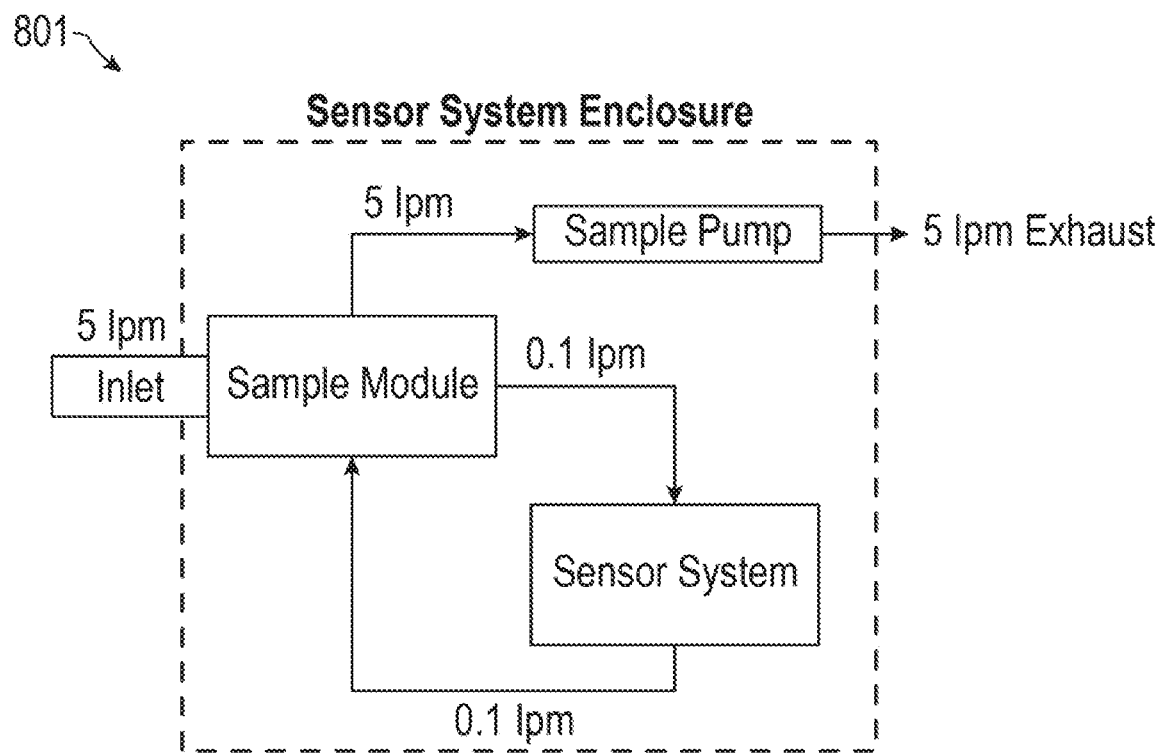
FIG. 30 is an illustration of a particular, non-limiting embodiment of a sensor system which may be utilized in the devices disclosed herein.

FIG. 30 is an illustration of a particular, non-limiting embodiment of a sensor system 801 which may be utilized in the devices disclosed herein. The sensor system exhaust 803 in this particular embodiment ties back into the main flow chamber, minimizing sensor pressure differential pumping requirements. The particular embodiment depicted has a 5 L/min flow rate.

In a preferred embodiment, the combination aerosol impactor/virtual impactor systems disclosed herein have a porous and/or sorbent coated collection surface that enables the simultaneous collection and pre-concentration of particles and vapors. The collection surface also preferably enables vaporization via thermal and ambient pressure reduction and subsequent analysis by a chemical detection system. The resultant vapor-only material is transferred through the porous collection surface into a minor flow gas for subsequent detection and identification by a chemical detector system. A pre-filter (which may be, for example, a traditional filter or size-selecting inertial separator) may be employed to prevent larger particles from entering the vaporization region.

The impaction nozzle is preferably equipped with a direct attachment impactor or virtual impaction receiver section to maintain alignment without stringent machining requirements. In a preferred embodiment, the impaction/collection surface section is attached to a desorption heater and minor flow sampling tube. The subunits are joined with a thread and retainer arrangement that allows for sufficient pressure to be applied to the outer edge of the collection surface to create a seal, thereby ensuring that all collected vapor enters the chemical analysis stream. Of course, one skilled in the art will appreciate that various sealings means may be utilized to similar effect. Thus, for example, instead of using the face seal approach depicted in the present embodiment, a suitable seal may instead be obtained through the proper use of O-rings, gaskets, taper-to-cone seals, and other suitable sealing means.

The system design preferably includes a single step alignment to maintain concentricity without multiple machining steps to minimize fabrication tolerances required with existing designs. The sampling tube includes a heater arrangement that applies sufficient thermal energy to the collection surface from the back to vaporize collected particulates. However, various heating means may be utilized to similar effect. Thus, for example, a suitable heating means may be incorporated into or coupled with the virtual impact nozzle. Similarly, heat may be applied from the front side of the collection surface, or even from within the collection surface (for example, through inductive or resistive heating).

The foregoing arrangement allows the collected particulates to pass through the collection surface into a low flow stream. This stream is further heated as it passes along the heater element, thus significantly increasing chemical transfer efficiency. A secondary heating method using optical heating techniques may provide sufficient energy to vaporize particles without, or in addition to, traditional conduction-based heating methods. The result is a highly concentrated, low volume air stream with concentrated vapors originating from the heated particulates or concentrated vapors.

In a preferred embodiment, an aerosol and enhanced sample module is disclosed herein samples at a variable flow rate from 1 to 10 LPM and concentrates an incoming sample by a factor of up to 100× over the ambient concentration (these values are based on a 100 mL/min sample flow, and could be even higher in the case of lower flow sensors; thus, for example, a 20 mL/min flow rate may concentrate an incoming sample by 400λ or more). The resultant, highly concentrated vapor is continually ported into a variable flow volume to pass to the detection system. The operation is analogous to continuous sampling, where the aerosol and enhanced sample module selectively collects the aerosol and immediately converts captured aerosol into vapors. Pulsed mode operation of the system is also possible, which increases the pre-concentration factor for both aerosols and vapors in an analogous manner to sorbent-based sampling techniques.

The system is preferably customizable at the design stage for cut points of 0.25 to 20 um particles, and retains some flexibility during operation by varying the sampling flow rate and/or by using pulsed operation. The unit is configured to report and accept commands via either direct or wireless connection using an Internet of Things (IoT)-based micro-Controller. This configuration facilitates remote monitoring and dynamic response in an integrated monitoring system.

The aerosol and enhanced sample modules disclosed herein may operate as high flow inlet, low flow outlet concentrators and vapor converters for chemical detection technologies. The core system is preferably comprised of four (5) main components, namely, a sample inlet, a sample chamber, a collection surface, a radiator assembly and a pump. All of these components may be operated by a simple micro-controller. The system may be connected to a variety of detectors based on various detector technologies, and may achieve a variety of operational parameters to meet the temperature, flow and pressure requirements of multiple systems.

The inlet 205 preferably facilitates remote sampling, either from the local environment, or via a longer sample length to a remote location. Here, it is noted that typical low-flow chemical detection systems suffer from significant transport losses over long distances. The sample lengths must then be augmented with heated lines to prevent sample loss from the area of interest, or must utilize externally mounted high flow sample pumps. By contrast, the aerosol and enhanced sample module flow rates in a device having the flow path depicted in FIG. 2 facilitate remote sampling by increasing the inlet flow, thus reducing sample latency and minimizing loss in the transport tubing.

An optional Inertial Separation Inlet (ISI) may be mounted on the collection system and may be used to protect the sensor from high particulate environments and to exclude particles larger than 10 μm without the use of a filter. The baseline ISI design preferably utilizes tailored air flow to limit the collection of particles larger than 10 microns without a filter. This feature helps to protect the collection system from blowing sand and highly contaminated environments without the added maintenance of commonly used filters. The ISI design may be tailored based on flow rate and desired cut point for particle size, extending the use of the aerosol and enhanced sample module to industrial applications where other sensors are inoperable.

In a preferred embodiment, the collection chamber provides a centralized location for size selection via inertial impaction, a sampling reservoir during pulsed operation, and an interface for optical sensing and/or system monitoring capabilities. The collector pre-heats the incoming air slightly to facilitate vaporization, and to minimize surface deposition (which is common in cold systems). Heating may be accomplished with embedded heating elements to enhance collection of vapors while minimizing surface contamination in high loading environments. The cut-point filter works on pre-heated air and deposits particles of the desired size onto the concentrator.

When operated in pulsed mode, vaporized chemicals release from the cutpoint filter, filling the volume collection chamber volume. Internal volume, weight, size, and configuration may be readily varied to accommodate detector parameters. For example, some embodiments ensure that pulsed mode operation will provide a stable concentration throughout the analysis period for the detection system. Other configurations may also enable variable path lengths within the chamber for optical-based measurement technologies.

The concentrator may be configured for a variety of operational modes, depending on the detection schema. In a preferred embodiment, when the concentrator is in flow-through-mode, it effectively pulls all particles (i.e., particles having dimensions of 2-10 micron) and vapors from a high flow stream (for example, 10 liters per minute (lpm)) into a centralized location where they are collected and vaporized. The resultant high concentration of vapor is then transferred to the detector at a substantially lower flow rate (such as, for example, 100 ml/min), thereby substantially enhancing chemical concentrations. In the case identified, all particles from 10 lpm concentrated into 100 ml/min will yield theoretical maximum concentration of 100 times the ambient concentration. However, system losses and chemical characteristics (such as, for example, boiling point) will impact the end performance.

In pulsed-mode, the vaporizer is only operated after a collection period. This allows the physical concentration of particles and vapors on the porous collection surface to be varied over time. Although $100\lambda$ and higher concentrations are possible in flow-through mode, substantially higher concentrations are possible when integrated over time when using pulsed mode prior to vaporization. The either case, the detection system samples the desorbed agent and preferably transports it to the detector via insulated (or heated) transfer lines to minimize losses due to surface deposition.

The system controller may be configured for local or remote operation. Settings may be hard wired or varied externally, based on input from a user or a detection system. The flow rates, temperatures of the collector and vaporizer are preferably adjustable to allow a user to monitor the conditions for proper operations. In as preferred embodiment, the controller can operate the sample module in 6 different modes.

Variations on collection efficiency and cutpoint diameter may be achieved using multiple methods, with the user changing each component easily using minimal tools. For example, increasing nozzle diameter with a constant flow increases the particle cutpoint (i.e. collecting only larger particles). Increasing the separation between in the inlet nozzle output and the collection surface by changing the amount it is engaged may also increase the cutpoint (collecting only larger particles). The system may be easily modified with single hardware changes (nozzle diameter, virtual impactor cone style, separation module (typically with different screen holder changes).

The system is preferably equipped with a pump which collects vapors and aerosols and guides them into the inlet at flows up to 10 L/min. The inlet gas stream separates and collects particles by accelerating the flow through a small orifice. Particles may then be separated via an inertial impaction nozzle located above a low flow air stream and heated surface. Once in contact with the surface, particles are vaporized.

Particles are collected when they cannot follow the bulk flow streamlines. The bulk airstream exits 90 degrees from the inlet and, based on the size of the particle, the momentum of the (typically 0.25 to 10 micron) aerosol particle forces it to continue a straight path and impinge upon the collection surface. Vapors also travel through the system and impinge the collection surface in this manner. The radiator inside of the front end heats the collection surface (preferably up to 300° C.) and vaporizes the aerosols.

The radiator inside of the front end heats the collection surface (preferably up to 350° C.) and vaporizes the aerosols. The vapors are then transported into the gas cell for analysis by the attached detection system. The 10 LPM of air that makes the right-hand turn without impinging on the collection media is exhausted or directed into the gas cell, depending on operational modes.

In a preferred embodiment, the front includes only 1 moving part. The front is preferably a small package. Thus, in a typical embodiment, the front end is a cylinder 5 cm diameter by 7 cm tall that weights 154 grams. The flexible design leverages advances in 3-D metal printing technology combined with a machined inlet nozzle, collection surface, radiator heater, exhaust ports, pumps and electronics.

The system may be mounted in either a vertical or horizontal configuration. Aerosols and vapor challenges may be connected directly to the inlet of the system via a ½ inch Swagelok fitting either straight up (as in FIG. 4) or with a right angle (as shown in FIG. 5). The ½ inch Swagelok may be a reduction style device. However, it is preferred to maximize the size of the fitting in order to minimize particle losses associated with bends and changes in inlet flow profiles. The straight connection shown in FIG. 4 is the preferred arrangement, but the right angle shown in FIG. 5 is also feasible to better allow the operator access to the screen and keypad control.

In a preferred embodiment, the system includes multiple modes of operation. The system may operate in a flow-through or in a pulsed mode, depending on the required concentration and on the tolerance or detection time requirements. In flow-through mode, gases are preferably heated slightly as they enter the gas cell, while aerosols are preferably impinged on a heated collection surface for vaporization prior to entering the cell. Flow-through mode provides significant concentration of particles, typically concentrating all particles in the targeted size range in a lower flow stream which may then be analyzed. Theoretical concentration factors of up to 100 or more may be possible, assuming minimal losses. Vapors are not concentrated in the system, but testing has indicated that the heated path for vapors results in an increased probability of detection (without wishing to be bound by theory, this is likely due to the increased mobility at higher temperatures).

In pulsed mode, the collection system may concentrate samples over time, further enhancing system sensitivity. The system may collect particles over a configurable period of time. For analysis, the collection pump is shut off to enable the resultant vapors to fill the vessel volume. Once off, the system rapidly heats all collected material, preferably with a combination of resistive and IR heating elements. The rapid heating volatilizes solid or liquid aerosols into vapors, which are then available for detection. For rapid detection and warning and site assessment requirements, the pulse time may be as short as 5 seconds and typically does not exceed 20 seconds, and for residual hazard/decontamination and low level chemical monitoring applications, this pulse time may be extended to 600 seconds or more as appropriate for the application.

The various modes of operation of a preferred (but non-limiting) embodiment of the system are identified below. Each mode is preferably selectable by sending a command string to the unit via a USB bus. For checkout and prototype operations, support software may be used to set the mode and read back the sensor values.

Idle mode (MODE=0) includes all temperatures and the pump in the off state. Readbacks will still provide status on each of the sensors, but no "operations" will occur.

Flow-through (mode=1) will apply the collection surface heater, housing heater, and pump control to maintain the setpoints (150° C., 100° C. and 100 mbar as a baseline).

Optical desorb (mode=2) will initiate a cycle of collection time and IR heater on time based on the specified preset values (i.e., 20 second collect, 10 second optical desorb). The collection surface heater will be maintained at a level below the setpoint (i.e., setpoint-50) during collection cycles.

Pulsed desorb (mode=3) provides a set of collections and pump off time during a conceptual sample from the chamber.

Rapid thermal ramp (mode=4) turns on the pump and applies the housing heaters and collection surface heaters to preset values above the setpoint values to drive off ultra-low volatility materials for detection. Preferably, detection occurs throughout this process.

Vapor (mode=5) provides the same parameters as flow through with the pump off. This maintains the heat in the housing and collection surface, but keeps the pump in an off state allowing the device to directly sample into the detector with a heated sample inlet (to improve chemical transfer efficiency).

The sample module is configured with a removable nozzle and collection surface that can be removed by an operator if needed due to wear and/or excessive contamination.

The controller may be operated via a suitable interface such as, for example, a universal serial bus (USB) port. Support software may be provided to control and monitor the aerosol and enhanced sample module, including the ability to set the temperatures and monitor the pressures in the system. Such software may run on a suitable operating system such as, for example, the Windows or Linux operating systems.

FIG. 7 depicts a screen shot of the Sample Module Controller for a particular, non-limiting embodiment of such software. As seen therein, the Sample Module Controller 701 in this particular embodiment provides a user interface that enables a user to control and/or monitor various features and operating parameters of the aerosol and enhanced sample module converter. These include fields for allowing the user to enter or adjust the collection surface setpoint (in ° C.), housing setpoint (in ° C.), pressure setpoint (in mBar), flash on time (in seconds), collect time (in seconds), and test pump duration (in seconds). Selectable options are also provided to enable the user to test a lamp in the device, select an operational mode (e.g., continuous or pulsed), enabling logging (for example, for troubleshooting purposes), and to connect or disconnect the device from WiFi communications.

The Sample Module Controller 701 also displays the current value or status of various operational parameters. These include, for example, an indication of whether the flash, pump, collection surface heater, and housing heater are on or off, the response status of the device, and the current number of packets. The Sample Module Controller 701 also displays the fault status of the flash, collection surface temperature, collection surface heat, pump, nozzle, filter (collection surface) and flow. The Sample Module Controller 701 further displays the current value of the collection surface temperature (in ° C.), the housing temperature (in ° C.), the filter pressure (in mBar), and the nozzle pressure (in mBar).

Normally, the aerosol and enhanced sample module will be controlled by the host sensor via the USB bus. An Interface Control document may be provided that describes all of the commands and response strings as well as the format of the data from the sensors. The aerosol and enhanced sample module controller preferably uses a USB/UART integrated circuit to present itself as a Virtual COM port to a host. In such an embodiment, the UART nominally operates at 57600 bps with 8 data bits, 1 start bit, 1 stop bit and no parity (8N1), but may be configured for operation to suite the host sensor needs. Also, the IoT capabilities of the aerosol and enhanced sample module controller may be used to monitor operation of the aerosol and enhanced sample module remotely. Existing web services may be utilized that allow data to be captured or graphed, or it may be streamed directly to a browser.

An example data package from a aerosol and enhanced sample module controller is shown below showing the timestamps and core ID of the controller (programed at the factory and specific to each board). The example shows the actual temperatures and pressures, the programmed temperatures and pressures, the status of the pumps and heaters, and the result of all fault checking. It also shows the firmware version and the serial number of the board, as well as the data added by the web services with the date/time stamp. {"data":"412,149,17,90,400,150,100,15,60,1,OFF, ON,ON,OFF,OK,OK,OK,OK, OK,OK,OK,2.11h,5, 144.528000","ttl":"60","published_at":"2016-08-29T20: 31:24.416Z","coreid";"23001c0007473531383838138"}

EXAMPLE 1

This example illustrates the operation of an aerosol and enhanced sample module in accordance with the teachings herein.

An experiment using 5 μm SYLOID© amorphous silica particles with 10% coverage of caffeine was performed in an aerosol chamber. A 5-minute pulse of particles followed by a two-step 8-minute pulse of particles was presented to the sensor. The sensor sampled at 5 LPM from the aerosol chamber.

The sensor response to the desorbed caffeine is depicted in FIG. 13. The response time and clear down times may be seen in the graphs. As seen therein, the particular embodiment of the aerosol and enhanced sample module used in this experiment took about 1 minute to start responding, and about 8 minutes to clear. Note that the integration of particles onto the concentrator causes the signal to lag behind the particle concentration.

Various substitutions and modifications to the devices and methodologies disclosed herein are possible without departing from the scope of the present disclosure. For example, various types of collection surfaces may be utilized in the devices and methodologies disclosed herein, and their structure, composition and porosity may be dictated, at least in part, by the intended use of the device. Preferably, the collection surface is a porous medium such as, for example, a filter medium, screen, frit, particle bed, or coil which is capable of collecting particulate matter thereon, while also allowing some fluidic flow through the medium. In some embodiments, the collection surface may be coated with a suitable sorbent.

The above description of the present invention is illustrative, and is not intended to be limiting. It will thus be appreciated that various additions, substitutions and modifications may be made to the above described embodiments without departing from the scope of the present invention. Accordingly, the scope of the present invention should be construed in reference to the appended claims.

What is claimed is:

1. A sampling system, comprising:
a collection chamber equipped with an inlet and first and second outlets;
a pump which creates a flow of fluid into said inlet from the ambient environment, wherein said collection chamber divides the flow of fluid into a first major flow of fluid which flows along a first flow path between said inlet and said first outlet, and a second minor flow of fluid which flows along a second flow path from said inlet and through said second outlet;
a collection surface disposed within said collection chamber and within the second flow path such that particles in the flow of fluid into said inlet impinge on said collection surface;
a heater which vaporizes particles that collect on said collection surface; and
an analyzer which analyzes the composition of second flow of fluid that emerges from said second outlet;
wherein said collection chamber further comprises a nozzle equipped with an orifice, wherein said nozzle has an interior surface which is conically shaped in a cross-section taken in a plane which includes said orifice and said inlet;
wherein said collection chamber further comprises (a) a collection surface holder which holds the collection surface in a spaced-apart relation to said nozzle;
wherein said collection surface holder comprises a first end which engages said nozzle, and a second end which holds said collection surface in a spaced-apart relation with respect to said nozzle;
wherein said collection surface holder comprises a first end which engages said nozzle, and a second end which holds said collection surface in a spaced-apart relation with respect to said nozzle, and a wall which extends between said first and second ends; and
wherein said wall has at least one opening therein.

2. The sampling system of claim 1, wherein said collection surface has a first major surface, wherein the flow of fluid in said first flow path impinges on said first major surface and travels in a direction parallel thereto, and wherein the flow of fluid in said second flow path travels through said first major surface.

3. The sampling system of claim 1, wherein the flow of fluid into the inlet travels along a first axis, wherein the flow of fluid out of the first outlet travels along a second axis, wherein the second axis is disposed at an angle $\emptyset_{21}$ with respect to said first axis, and wherein $|\emptyset_{21}|$ is within the range of 60° to 120°.

4. The sampling system of claim 3, wherein the flow of fluid out of the second outlet travels along a third axis, wherein the third axis is disposed at an angle $\emptyset_{31}$ with respect to said first axis, and wherein $|\emptyset_{31}|$ is within the range of 0° to 30°.

5. The sampling system of claim 1, wherein said inlet is equipped with a nozzle having first and second apertures and having a fluidic flow path therethrough which extends from said first aperture to said second aperture, wherein said first aperture has a first diameter in a first plane orthogonal to said flow path, wherein said second aperture has a second diameter in a second plane orthogonal to said flow path, and wherein said first diameter is larger than said second diameter.

6. The sampling system of claim 1, wherein said analyzer performs at least one analysis selected from the group consisting of mass spectrometry, ion mobility spectrometry, infrared spectrometry, and Fourier transform infrared spectrometry.

7. The sampling system of claim 1, wherein said collection surface is disposed within a chamber having a frustoconical shape and having first and second openings, wherein said first opening is smaller than said second opening, and wherein said second minor flow enters said chamber through said first opening.

8. The sampling system of claim 1, wherein $r_{12}$ is the ratio of the volumetric rate of fluid along said first flow path to the volumetric ratio of fluid along said second flow path, and wherein $r_{12}$ is within the range of 5 to 500.

9. The sampling system of claim 1, wherein said collection surface holder further comprises at least one opening disposed between said first and second ends.

10. The sampling system of claim 9, wherein said collection surface holder further comprises first and second longitudinal elements, wherein each of said first and second longitudinal elements is attached at a first end thereof to the first end of said collection surface holder, and wherein each of said first and second longitudinal elements is attached at a second end thereof to the second end of said collection surface holder.

11. The sampling system of claim 1, wherein said collection surface holder comprises a first annulus which engages said nozzle, a second annulus which holds said collection surface in a spaced-apart relation with respect to said nozzle, and a support element which attaches said first annulus to said second annulus.

12. The sampling system of claim 1, further comprising a heating device which applies heat to said collection surface.

13. The sampling system of claim 12, wherein said collection surface holder is disposed between said nozzle and said heating device.

14. The sampling system of claim 13, wherein said second end of said collection surface holder pressingly engages said heating device.

15. The sampling system of claim 1, wherein said collection surface is porous, and wherein said second flow of fluid extends through said collection surface.

16. The sampling system of claim 15, further comprising:
a heating device which applies heat to said collection surface, wherein said heating device has an interior channel therein, and wherein said second flow of fluid extends through said interior channel.

17. The sampling system of claim 16, wherein said heating device comprises a cylindrical heater concentrically disposed within a cylindrical housing, wherein the radius of said cylindrical heater is smaller than the radius of said cylindrical housing, and wherein the space between said cylindrical heater and said cylindrical housing forms a portion of said second flow path.

18. The sampling system of claim 1, wherein said collection surface has a first major surface, wherein the flow of fluid in said first flow path impinges on said first major surface and travels in a direction parallel thereto, and wherein the flow of fluid in said second flow path travels through said first major surface.

19. The sampling system of claim 1, wherein the flow of fluid into the inlet travels along a first axis, wherein the flow of fluid out of the first outlet travels along a second axis, wherein the second axis is disposed at an angle $\emptyset_{21}$ with respect to said first axis, and wherein $|\emptyset_{21}|$ is within the range of 60° to 120°.

20. A sampling system, comprising:
   a collection chamber equipped with an inlet and first and second outlets;
   a pump which creates a flow of fluid into said inlet from the ambient environment, wherein said collection chamber divides the flow of fluid into a first major flow of fluid which flows along a first flow path between said inlet and said first outlet, and a second minor flow of fluid which flows along a second flow path from said inlet and through said second outlet;
   a collection surface disposed within said collection chamber and within the second flow path such that particles in the flow of fluid into said inlet impinge on said collection surface;
   a heater which vaporizes particles that collect on said collection surface; and
   an analyzer which analyzes the composition of second flow of fluid that emerges from said second outlet;
   wherein said collection chamber further comprises a nozzle equipped with an orifice, wherein said nozzle has an interior surface which is conically shaped in a cross-section taken in a plane which includes said orifice and said inlet;
   wherein said collection chamber further comprises (a) a collection surface holder which holds the collection surface in a spaced-apart relation to said nozzle;
   wherein said collection surface holder comprises a first end which engages said nozzle, and a second end which holds said collection surface in a spaced-apart relation with respect to said nozzle;
   wherein said collection surface holder comprises a first annulus which engages said nozzle, a second annulus which holds said collection surface in a spaced-apart relation with respect to said nozzle, and a support element which attaches said first annulus to said second annulus.

* * * * *